(12) United States Patent
Chuntharapai et al.

(10) Patent No.: US 12,139,551 B2
(45) Date of Patent: Nov. 12, 2024

(54) ANTI-IDO ANTIBODY AND USES THEREOF

(71) Applicant: BRISTOL-MYERS SQUIBB COMPANY, Princeton, NJ (US)

(72) Inventors: Anan Chuntharapai, Daly City, CA (US); Paul Blaine Mesko, Redwood City, CA (US); Thomas E. Spires, Jr., Howell, NJ (US); Gaby A. Terracina, Metuchen, NJ (US); Xi-Tao Wang, Wellesley, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 699 days.

(21) Appl. No.: 17/299,038

(22) PCT Filed: Dec. 2, 2019

(86) PCT No.: PCT/US2019/063910
§ 371 (c)(1),
(2) Date: Jun. 2, 2021

(87) PCT Pub. No.: WO2020/117627
PCT Pub. Date: Jun. 11, 2020

(65) Prior Publication Data
US 2021/0403602 A1 Dec. 30, 2021

Related U.S. Application Data

(60) Provisional application No. 62/776,057, filed on Dec. 6, 2018, provisional application No. 62/774,696, filed on Dec. 3, 2018.

(51) Int. Cl.
| | | |
|---|---|---|
| *C07K 16/00* | (2006.01) | |
| *A61P 35/00* | (2006.01) | |
| *C07K 16/40* | (2006.01) | |
| *G01N 1/30* | (2006.01) | |
| *G01N 33/574* | (2006.01) | |

(52) U.S. Cl.
CPC .............. *C07K 16/40* (2013.01); *A61P 35/00* (2018.01); *G01N 1/30* (2013.01); *G01N 33/57496* (2013.01); *C07K 2317/565* (2013.01); *G01N 2001/302* (2013.01); *G01N 2333/90241* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,634,665 A | 1/1987 | Axel et al. | |
| 4,683,195 A | 7/1987 | Mullis et al. | |
| 4,816,567 A | 3/1989 | Cabilly et al. | |
| 5,179,017 A | 1/1993 | Axel et al. | |
| 5,225,539 A | 7/1993 | Winter | |
| 5,530,101 A | 6/1996 | Queen et al. | |
| 5,585,089 A | 12/1996 | Queen et al. | |
| 5,693,762 A | 12/1997 | Queen et al. | |
| 6,180,370 B1 | 1/2001 | Queen et al. | |
| 6,989,452 B2 | 1/2006 | Ng et al. | |
| 7,087,600 B2 | 8/2006 | Ng et al. | |
| 7,129,261 B2 | 10/2006 | Ng et al. | |
| 2006/0004081 A1 | 1/2006 | Chen et al. | |
| 2006/0024317 A1 | 2/2006 | Boyd et al. | |
| 2006/0247295 A1 | 11/2006 | Gangwar et al. | |

FOREIGN PATENT DOCUMENTS

| | | |
|---|---|---|
| WO | 199517886 A1 | 7/1995 |
| WO | 199929310 A2 | 6/1999 |
| WO | 2002096910 A1 | 12/2002 |
| WO | 2004094409 A1 | 11/2004 |
| WO | 2007038658 A2 | 4/2007 |
| WO | 2007051081 A1 | 5/2007 |
| WO | 2007059404 A2 | 5/2007 |
| WO | 2008083312 A2 | 7/2008 |
| WO | 2008103693 A2 | 8/2008 |
| WO | 2009059278 A1 | 5/2009 |
| WO | 2015181266 A1 | 12/2015 |
| WO | 2016073770 A1 | 5/2016 |

OTHER PUBLICATIONS

Altschul, Stephen F. et al., "Basic Local Alignment Search Tool", J. Mol. Biol., vol. 215, pp. 403-410, 1990.

Altschul, Stephen F. et al., "Gapped BLAST and PSI-BLAST: a new generation of protein database search programs", Nucleic Acids Research, vol. 25, No. 17, pp. 3389-3402, 1997.

Anonymous: "Anti-IDO, clone 1F8.2", Oct. 2010 (Oct. 1, 2010), XP55203301, Retrieved fro the Internet:URL:https://www.merckmillipore.com/NL/en/product/Anti-IDO-Antibody-clone-1F8.2,MM NF-MAB10009 [retrieved on Jul. 17, 2015] 1-34—The whole document.

Anonymous: "Anti-Indoleaine 2, 3-dioxygenase antibody ab134197",Jul. 3, 2015 (Jul. 3, 2015), XP55203087, Retrieved from the Internet:URL:http://www.abcam.com/Indolea ine-2-3-dioxygenase-antibody-ab134197.pdf [retrieved on Jul. 17, 2015—The whole document.

Anonymous: "IDO1 purified MaxPab rabbit polyclonal antibody (D03P)", www.abnova.com, May 21, 2016 (May 21, 2016), pp. 1-2,XP55671153, Retrieved from the Internet: URL:https://www.abnova.com/PDFServer/outputs/H00003620-D03P.pdf [retrieved on Feb. 24, 2020]—A—The whole document.

(Continued)

Primary Examiner — Mark Halvorson

(74) Attorney, Agent, or Firm — Bing Hai

(57) ABSTRACT

The disclosure provides antibodies that specifically bind human IDO and methods of use thereof. In some aspects, the disclosure is directed to methods of detecting IDO in a biological sample comprising contacting the biological sample with an antibody described herein.

Figure 2:
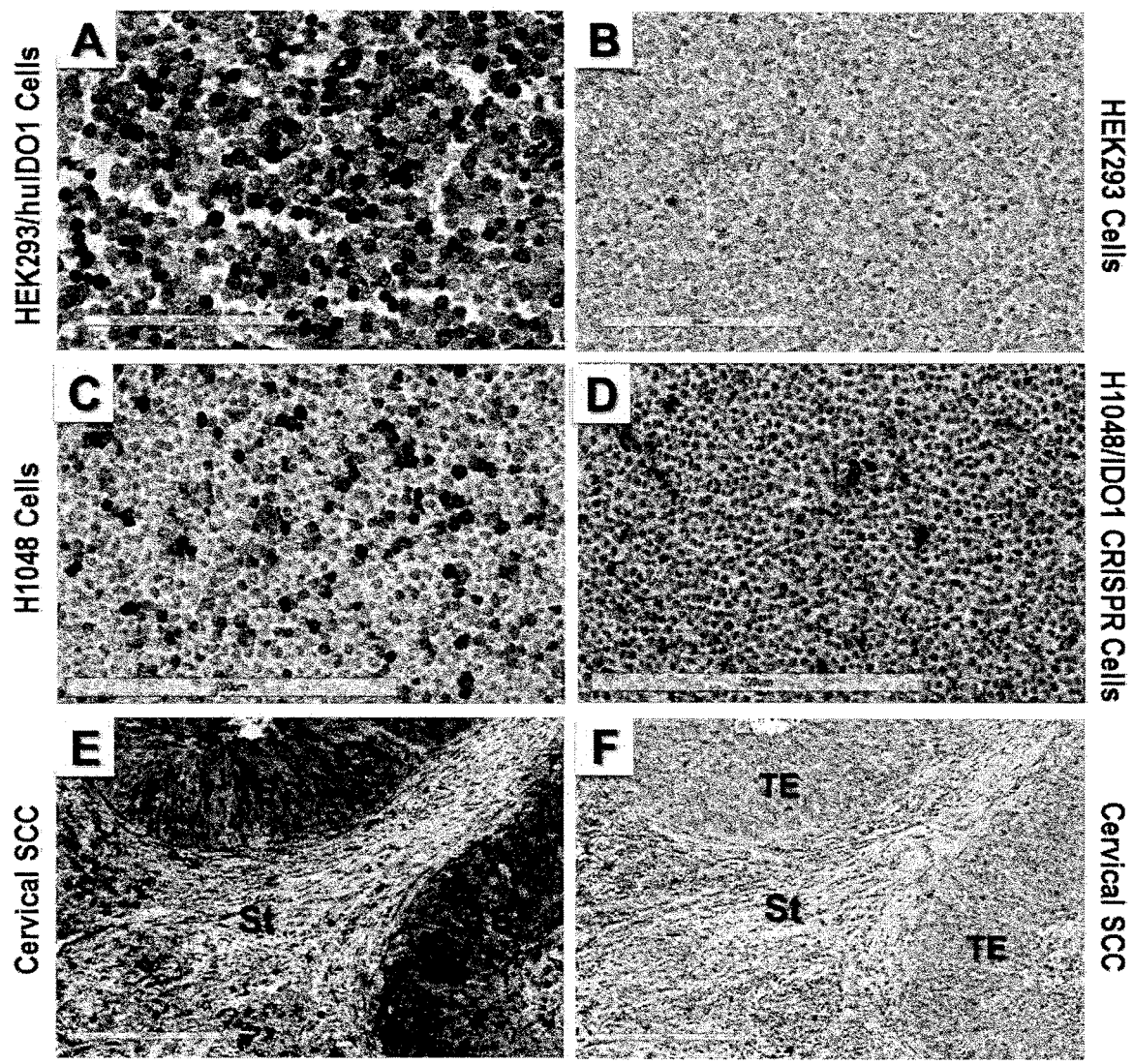

35 Claims, 5 Drawing Sheets
Specification includes a Sequence Listing.

(56) References Cited

OTHER PUBLICATIONS

Anonymous: "Purified anti-IDOI Antibody", www.biolegend.com, Jan. 23, 2017 (Jan. 23, 2017), pp. 1-2, XP55671160, Retrieved from the Internet: URL:https://www.biolegend.co /en-us/global-elents/pdf-popup/purified-anti-idol-antibody-14039?filename=Purified%20anti -ID01% 20Antibody.pdf&pdfgen=true [retrieved on Feb. 24, 2020—The whole document.

Anonymous: "Rabbit Anti-Human IDO-1 Monoclonal Antibody (Clone SP260)", Jan. 1, 2018 (Jan. 1, 2018), pp. 1-2, XP055671063, Retrieved from the Internet: URL:https://lifescience.roche.co /content/dam/RMS/1ifescience/Documents/PDF/M560_RUOA. pdfretrieved on Feb. 21, 2020—The whole document.

Ausubel, F.M., et al. "Short Protocols in Molecular Biology—A Compendium of Methods" from Current Protocols in Molecular Biology, Greene Publishing Associates and Wiley-Interscience, pp. 1-3, 1989.

Bird et al., "Single-Chain Antigen-Binding Proteins", Science, vol. 242 , pp. 423-426, 1988.

Brandacher, Gerald et al., PrognosticValue of Indoleamine 2,3-Dioxygenase Expression in Colorectal Cancer: Effect on Tumor-Infiltrating T Cells, Clin. Cancer Research, vol. 12(4), pp. 1144-1151, 2006.

Brummell, David A. et al., "Probing the Combining Site of an Anti-Carbohydrate Antibody by Saturation-Mutagenesis: Role of the Heavy-Chain CDR3 Residues", Biochemistry, vol. 32, pp. 1180-1187, 1993.

Burks, Elizabeth A. et al., "In vitro scanning saturation mutagenesis of an antibody binding pocket", Proc. Natl. Acad. Sci. USA, vol. 94, pp. 412-417, 1997.

Carvajal-Hausdorf, Daniel E. et al., "Objective measurement and clinical significance of IDO1 protein in hormone receptor-positive breast cancer", Journal for Immuno Therapy of Cancer, vol. 5:81, pp. 1-9, 2017.

Cheung, Ramsey C. et al., "Epitope-Specific Antibody Response to the Surface Antigen of Duck Hepatitis B Virus in Infected Ducks", Virology, vol. 176, pp. 546-552, 1990.

Crooks, Stanley, T., Antisense drug Technology: Principles, strategies and applications, 2nd Edition, CRC Press, pp. 1-5, 2007.

D.N. Glover, "DNA Cloning, vols. I and II—a practical approach", Cancer Research Campaign, Eukaryotic Molecular Genetics Research Group, Department of Biochemistry, Imperial College of Science and Technology, London, SW7 2AZ, UK, 1985.

F. Ausubel, et al., "Current Protocols in Molecular Biology", John Wiley and Sons, Baltimore, MD—1994-1998.

Freshney, R. Ian, Culture of Animal Cells—A Manual of Basic Technique, Department of Medical Oncology Cancer Research Campaign Laboratories, University of Glasgow, Alan R. Liss, Inc., New York, pp. 1-10, 1987.

Gait, M.J., "Oligonucleotide Synthesis—a practical approach", MRC Laboratory of Molecular Biology, Hills Road, Cambridge CB2 2QH, England, IRL Press Limited, 1984.

Goeddel, David V., Gene Expression Technology. Methods in Enzymology 185, Academic Press, San Diego, CA (1990).

Greenfield, Edward A., "Antibodies—A Laboratory Manual"—Second Edition, Cold Spring Harbor Laboratory Press, Cold Spring Harbor, New York, 2014—(please note—Harlow and Lane reference, Antibodies: A Laboratory Manual, Cold Spring Harbor Press (1988) was not available.

Hames, B.D., et al., "Transcription and Translation—a practical approach", Department of Biochemistry, University of Leeds, Leeds, England, IRL Press Limited, 1984.

Harlow, Ed and David Lane, Cold Spring Harb Protoc; doi: 10.1101/pdb.prot4277 , pp. 1-2, 2006.

Huston, James S., et al., Protein Engineering of Antibody Binding Sites: Recovery of Specific Activity in an Anti-Digoxin Single-Chain Fv Analogue Produced In *Escherichia coli*, Proc. Natl. Acad. Sci USA, vol. 85, pp. 5879-5883, 1988.

Iversen, Trine Zeeberg et al., "Long-lasting Disease Stabilization in the Absence of Toxicity in Metastatic Lung Cancer Patients Vaccinated with an Epitope Derived from Indoleamine 2,3 Dioxygenase", Clin. Cancer Res; vol. 20, No. 1, pp. 221-232, 2014—Published OnlineFirst Nov. 11, 2013; DOI: 10. 1158/1078-0432. CCR-13-1560.

Johnson, Douglas B. et al., "Quantitative Spatial Profiling of PD-1/PD-L1 Interaction and HLA-DR/IDO-1 Predicts Improved Outcomes of Anti-PD-1 Therapies in Metastatic Melanoma", Clin. Cancer Res; vol. 24, No. 21, pp. 5250-5260, 2018.

Juo, Pei-Show, "The Concise Dictionary of Biomedicine and Molecular Biology", 2nd edition, 2002, CRC Press.

Kabat, E.A. et al., Sequences of Proteins of Immunological Interest, Fifth Edition, U.S. Department of Health and Human Services, NIH Publication, vol. 91-3242, pp. 1-8, 1991.

Kaufman, Randal J. et al., "Amplification and Expression of Sequences Cotransfected with a Modular Dihydrofolate Reductase Complementary DNA Gene", J. Mol. Biol., vol. 159, pp. 601-621, 1982. (Dear Mr. Robert, this article shows vol. 159 not "759" as shown in the Specification).

Kirkland, T.N. et al., "Analysis of the fine specificity and cross-reactivity of monoclonal anti-lipid A antibodies", The Journal of Immunology, vol. 137, No. 11, pp. 3614-3619, 1986.

Kobayashi, Hiroyuki et al., "Tryptophan H33 plays an important role in pyrimidine (6-4) pyrimidone photoproduct binding by a high-affinity antibody", Protein Engineering, vol. 12, No. 10, pp. 879-884, 1999.

Kozuma, Yuka et al., "Indoleamine 2,3-dioxygenase 1 and programmed cell death-ligand 1 co-expression correlates with aggressive features in lung adenocarcinoma", European Journal of Cancer, vol. 101, pp. 20-29, 2018.

Lackie, J.M. et al., "The Dictionary of Cell and Molecular Biology", 3rd ed., Academic Press, 1999.

Liu, Ming et al., "Targeting the IDO1 pathway in cancer: from bench to bedside", Journal of Hematology & Oncology, vol. 11:100, pp. 1-12, 2018.

Lonberg, "Human antibodies from transgenic animals", Nature Biotechnology, vol. 23 (9), pp. 1117-1125, 2005.

Mayer, R.J. et al., "Immunochemical Methods in Cell and Molecular Biology", Academic Press, London, pp. 1-3, 1987.

McCafferty, John et al., "Phage antibodies: filamentous phage displaying antibody variable domains" Nature, vol. 348, pp. 552-554, 1990.

Miller, Jeffrey H., and Calos, Michele P., "Gene Transfer Vectors for Mammalian Cells", Cold Spring Harbor Laboratory, 1987.

Moldenhauer, G. et al., "Identity of HML-1 Antigen on IntestinalIntraepithelial T Cells and of B-ly7 Antigen on Hairy Cell Leukaemia" Scand. J. Immunol., vol. 32, pp. 77-82, 1990.

Morel, G.A. et al., "Monoclonal Antibodies to Bovine Serumalbumin: Affinity and Specificity Determinations", Molecular Immunology, vol. 25, No. 1, pp. 7-15, 1988.

Morris, G.E., "Epitope Mapping Protocols in Methods in Molecular Biology", vol. 66, 1996.

Myers, Eugene W. et al., "Optimal alignments in linear space" Cabios, vol. 4, No. 1, pp. 11-17, 1988.(Dear Mr. Robert, the journal article I found has all this information with the exception for the year. The article is (1988) not 1989. Please advise).

Needleman, Saul B. et al., "A General Method Applicable to the Search for Similarities in the Amino Acid Sequence of Two Proteins", J. Mol. Biol. vol. 48, pp. 443-453, 1970.

Perbal—"A Practical Guide to Molecular Cloning; the treatise", Methods In Enzymology, Academic Press, Inc., N.Y., 1984.

Sambrook, J. et al., "Molecular Cloning, A Laboratory Manual", Cold Spring Harbor Press, Plainview, NY (1989).

Senter, Peter D., "Potent antibody drug conjugates for cancer therapy", Current Opinion in Chemical Biology, vol. 13, pp. 235-244, 2009.

Stahli, C. et al., "Distinction of Epitopes by Monoclonal Antibodies", Methods in Enzymology, vol. 92, pp. 242-253, 1983.

Takebe, Yutaka et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, vol. 8, No. 1, pp. 466-472, 1988.

The "Oxford Dictionary of Biochemistry and Molecular Biology", Revised 2000, Oxford University Press.

(56) References Cited

OTHER PUBLICATIONS

Urlaub, Gail et al., "Isolation of Chinese hamster cell mutants deficient in dihydrofolate reductase activity", Proc. Natl. Acad. Sci. USA, vol. 77, No. 7, pp. 4216-4220, 1980.
Ward, E. Sally et al., "Binding activities of a repertoire of single immunoglobulin variable domains secreted from *Escherichia coli*", Nature, vol. 341, pp. 544-546, 1989.
Weir and Blackwell, eds., "Handbook of Experimental Immunology", vols. I-IV; Manipulating the Mouse Embryo, Cold Spring Harbor Laboratory Press, Cold Spring Harbor, N.Y., 1986.
Woodward, J., "Immobilised Cells and Enzymes—a practical approach", IRL Press Limited, Washington, DC, pp. 1-2, 1986.
Mar. 20, 2020_International PCT Search Report Dated Mar. 20, 2020.

1E7 Heavy chain amino acid sequence (SEQ ID NO: 4)

FR1-CDR1-FR2-CDR2-FR3-CDR3-FR4

QVQLQQSGAELAKPGASVKMSCKTSGYTFTSYWMHWVKQRPGQGLEWIGYINPTTGYTDCNQKFKDK
                                CDR1                                CDR2

ATLTADKSSNTAYLQLSSLTSEDSAVYYCARSAMFGRGWGQGTTLTVSS
                                    CDR3

1E7 Light chain amino acid sequence (SEQ ID NO: 6)

FR1-CDR1-FR2-CDR2-FR3-CDR3-FR4

DVVMTQTPLTLSVTIGQPASISCKSSQSLLHSDGKTYLNWLLQRPGQSPKRLIYLVSKLDSGVPDRF
                              CDR1                                  CDR2

TGSGSGTDFTLKISRVEAEDLGVYYCWQGTHFPQTFGGGSKLEIK
                                  CDR3

Figure 1

SEQUENCE LISTING

```
<160> NUMBER OF SEQ ID NOS: 16

<210> SEQ ID NO 1
<211> LENGTH: 403
<212> TYPE: PRT
<213> ORGANISM: Homo sapiens

<400> SEQUENCE: 1

Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Lys Asp Pro Asn Lys Pro Leu Thr
    130                 135                 140

Tyr Glu Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
        195                 200                 205
```

```
Lys Ala Leu Gln Val Phe His Gln Ile His Asp His Val Asn Pro Lys
            210                 215                 220
Ala Phe Phe Ser Val Leu Arg Ile Tyr Leu Ser Gly Trp Lys Gly Asn
225                 230                 235                 240
Pro Gln Leu Ser Asp Gly Leu Val Tyr Glu Gly Phe Trp Glu Asp Pro
                245                 250                 255
Lys Glu Phe Ala Gly Gly Ser Ala Gly Gln Ser Ser Val Phe Gln Cys
                260                 265                 270
Phe Asp Val Leu Leu Gly Ile Gln Gln Thr Ala Gly Gly His Ala
                275                 280                 285
Ala Gln Phe Leu Gln Asp Met Arg Arg Tyr Met Pro Pro Ala His Arg
            290                 295                 300
Asn Phe Leu Cys Ser Leu Glu Ser Asn Pro Ser Val Arg Glu Phe Val
305                 310                 315                 320
Leu Ser Lys Gly Asp Ala Gly Leu Arg Glu Ala Tyr Asp Ala Cys Val
                325                 330                 335
Lys Ala Leu Val Ser Leu Arg Ser Tyr His Leu Gln Ile Val Thr Lys
            340                 345                 350
Tyr Ile Leu Ile Pro Ala Ser Gln Gln Pro Lys Glu Asn Lys Thr Ser
                355                 360                 365
Glu Asp Pro Ser Lys Leu Glu Ala Lys Gly Thr Gly Thr Asp Leu
370                 375                 380
Met Asn Phe Leu Lys Thr Val Arg Ser Thr Thr Glu Lys Ser Leu Leu
385                 390                 395                 400
Lys Glu Gly

<210> SEQ ID NO 2
<211> LENGTH: 423
<212> TYPE: PRT
<213> ORGANISM: Homo sapiens

<400> SEQUENCE: 2

Met Gly Ser Ser His His His His His His Ser Ser Gly Leu Val Pro
1               5                   10                  15
Arg Gly Ser His Met Ala His Ala Met Glu Asn Ser Trp Thr Ile Ser
                20                  25                  30
Lys Glu Tyr His Ile Asp Glu Glu Val Gly Phe Ala Leu Pro Asn Pro
            35                  40                  45
Gln Glu Asn Leu Pro Asp Phe Tyr Asn Asp Trp Met Phe Ile Ala Lys
    50                  55                  60
His Leu Pro Asp Leu Ile Glu Ser Gly Gln Leu Arg Glu Arg Val Glu
65                  70                  75                  80
Lys Leu Asn Met Leu Ser Ile Asp His Leu Thr Asp His Lys Ser Gln
                85                  90                  95
Arg Leu Ala Arg Leu Val Leu Gly Cys Ile Thr Met Ala Tyr Val Trp
            100                 105                 110
Gly Lys Gly His Gly Asp Val Arg Lys Val Leu Pro Arg Asn Ile Ala
        115                 120                 125
Val Pro Tyr Cys Gln Leu Ser Lys Lys Leu Glu Leu Pro Pro Ile Leu
    130                 135                 140
Val Tyr Ala Asp Cys Val Leu Ala Asn Trp Lys Lys Lys Asp Pro Asn
145                 150                 155                 160
Lys Pro Leu Thr Tyr Glu Asn Met Asp Val Leu Phe Ser Phe Arg Asp
                165                 170                 175
```

```
Gly Asp Cys Ser Lys Gly Phe Phe Leu Val Ser Leu Leu Val Glu Ile
            180                 185                 190

Ala Ala Ala Ser Ala Ile Lys Val Ile Pro Thr Val Phe Lys Ala Met
            195                 200                 205

Gln Met Gln Glu Arg Asp Thr Leu Leu Lys Ala Leu Leu Glu Ile Ala
210                 215                 220

Ser Cys Leu Glu Lys Ala Leu Gln Val Phe His Gln Ile His Asp His
225                 230                 235                 240

Val Asn Pro Lys Ala Phe Phe Ser Val Leu Arg Ile Tyr Leu Ser Gly
                245                 250                 255

Trp Lys Gly Asn Pro Gln Leu Ser Asp Gly Leu Val Tyr Glu Gly Phe
            260                 265                 270

Trp Glu Asp Pro Lys Glu Phe Ala Gly Gly Ser Ala Gly Gln Ser Ser
            275                 280                 285

Val Phe Gln Cys Phe Asp Val Leu Leu Gly Ile Gln Gln Thr Ala Gly
290                 295                 300

Gly Gly His Ala Ala Gln Phe Leu Gln Asp Met Arg Arg Tyr Met Pro
305                 310                 315                 320

Pro Ala His Arg Asn Phe Leu Cys Ser Leu Glu Ser Asn Pro Ser Val
                325                 330                 335

Arg Glu Phe Val Leu Ser Lys Gly Asp Ala Gly Leu Arg Glu Ala Tyr
            340                 345                 350

Asp Ala Cys Val Lys Ala Leu Val Ser Leu Arg Ser Tyr His Leu Gln
            355                 360                 365

Ile Val Thr Lys Tyr Ile Leu Ile Pro Ala Ser Gln Gln Pro Lys Glu
370                 375                 380

Asn Lys Thr Ser Glu Asp Pro Ser Lys Leu Glu Ala Lys Gly Thr Gly
385                 390                 395                 400

Gly Thr Asp Leu Met Asn Phe Leu Lys Thr Val Arg Ser Thr Thr Glu
                405                 410                 415

Lys Ser Leu Leu Lys Glu Gly
            420

<210> SEQ ID NO 3
<211> LENGTH: 348
<212> TYPE: DNA
<213> ORGANISM: Mus musculus

<400> SEQUENCE: 3
caggtccagc ttcagcagtc tggggctgaa ctggcaaaac ctggggcctc agtgaagatg      60
tcctgcaaga cttctggcta cacctttact agctactgga tgcactgggt aaaacagagg     120
cctggacagg gtctggaatg gattggatac attaatccta ccactggtta tactgactgc     180
aatcagaagt tcaaggacaa ggccacattg actgcagaca gtcctccaa cacagcctac      240 ttgcaactga gcagcctgac atctgaggac tctgcagtct attactgtgc cagatcggct     300
atgtttggta gggggtgggg ccaaggcacc actctcacgg tctcctca                  348

<210> SEQ ID NO 4
<211> LENGTH: 116
<212> TYPE: PRT
<213> ORGANISM: Mus musculus

<400> SEQUENCE: 4

Gln Val Gln Leu Gln Gln Ser Gly Ala Glu Leu Ala Lys Pro Gly Ala
1               5                   10                  15
```

Ser Val Lys Met Ser Cys Lys Thr Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Thr Thr Gly Tyr Thr Asp Cys Asn Gln Lys Phe
    50                  55                  60

Lys Asp Lys Ala Thr Leu Thr Ala Asp Lys Ser Ser Asn Thr Ala Tyr
65                  70                  75                  80

Leu Gln Leu Ser Ser Leu Thr Ser Glu Asp Ser Ala Val Tyr Tyr Cys
                85                  90                  95

Ala Arg Ser Ala Met Phe Gly Arg Gly Trp Gly Gln Gly Thr Thr Leu
            100                 105                 110

Thr Val Ser Ser
        115

<210> SEQ ID NO 5
<211> LENGTH: 336
<212> TYPE: DNA
<213> ORGANISM: Mus musculus

<400> SEQUENCE: 5
gatgttgtga tgacccagac tccactcact ttgtcggtta ccattggaca accagcctcc      60
atctcttgca agtcaagtca gagcctctta catagtgatg aaagacata tttgaattgg     120 ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgtt ggcaaggtac acatttcct     300 cagacgttcg gtggaggctc caagctggaa atcaaa                               336

<210> SEQ ID NO 6
<211> LENGTH: 112
<212> TYPE: PRT
<213> ORGANISM: Mus musculus

<400> SEQUENCE: 6

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Ser Lys Leu Glu Ile Lys
            100                 105                 110

<210> SEQ ID NO 7
<211> LENGTH: 5
<212> TYPE: PRT
<213> ORGANISM: Mus musculus

<400> SEQUENCE: 7

```
Ser Tyr Trp Met His
1               5
```

<210> SEQ ID NO 8
<211> LENGTH: 17
<212> TYPE: PRT
<213> ORGANISM: Mus musculus

<400> SEQUENCE: 8

```
Tyr Ile Asn Pro Thr Thr Gly Tyr Thr Asp Cys Asn Gln Lys Phe Lys
1               5                   10                  15

Asp
```

<210> SEQ ID NO 9
<211> LENGTH: 7
<212> TYPE: PRT
<213> ORGANISM: Mus musculus

<400> SEQUENCE: 9

```
Ser Ala Met Phe Gly Arg Gly
1               5
```

<210> SEQ ID NO 10
<211> LENGTH: 16
<212> TYPE: PRT
<213> ORGANISM: Mus musculus

<400> SEQUENCE: 10

```
Lys Ser Ser Gln Ser Leu Leu His Ser Asp Gly Lys Thr Tyr Leu Asn
1               5                   10                  15
```

<210> SEQ ID NO 11
<211> LENGTH: 7
<212> TYPE: PRT
<213> ORGANISM: Mus musculus

<400> SEQUENCE: 11

```
Leu Val Ser Lys Leu Asp Ser
1               5
```

<210> SEQ ID NO 12
<211> LENGTH: 9
<212> TYPE: PRT
<213> ORGANISM: Mus musculus

<400> SEQUENCE: 12

```
Trp Gln Gly Thr His Phe Pro Gln Thr
1               5
```

<210> SEQ ID NO 13
<211> LENGTH: 439
<212> TYPE: PRT
<213> ORGANISM: Mus musculus

<400> SEQUENCE: 13

```
Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Thr Thr Gly Tyr Thr Asp Cys Asn Gln Lys Phe
    50                  55                  60
```

Lys Asp Lys Ala Thr Leu Thr Ala Asp Lys Ser Ser Asn Thr Ala Tyr
65                  70                  75                  80

Leu Gln Leu Ser Ser Leu Thr Ser Glu Asp Ser Ala Val Tyr Tyr Cys
            85                  90                  95

Ala Arg Ser Ala Met Phe Gly Arg Gly Trp Gly Gln Gly Thr Thr Leu
            100                 105                 110

Thr Val Ser Ser Ala Lys Thr Thr Pro Pro Ser Val Tyr Pro Leu Ala
            115                 120                 125

Pro Gly Ser Ala Ala Gln Thr Asn Ser Met Val Thr Leu Gly Cys Leu
130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
            165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
            195                 200                 205

Val Asp Lys Lys Ile Val Pro Arg Asp Cys Gly Cys Lys Pro Cys Ile
210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
            245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
            275                 280                 285

Phe Asn Ser Thr Phe Arg Ser Val Ser Glu Leu Pro Ile Met His Gln
290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
            325                 330                 335

Lys Ala Pro Gln Val Tyr Thr Ile Pro Pro Pro Lys Glu Gln Met Ala
            340                 345                 350

Lys Asp Lys Val Ser Leu Thr Cys Met Ile Thr Asp Phe Phe Pro Glu
            355                 360                 365

Asp Ile Thr Val Glu Trp Gln Trp Asn Gly Gln Pro Ala Glu Asn Tyr
            370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
            405                 410                 415

Thr Cys Ser Val Leu His Glu Gly Leu His Asn His Thr Glu Lys
            420                 425                 430

Ser Leu Ser His Ser Pro Gly
            435

<210> SEQ ID NO 14
<211> LENGTH: 1317
<212> TYPE: DNA
<213> ORGANISM: Mus musculus

<400> SEQUENCE: 14

```
caggtccagc ttcagcagtc tggggctgaa ctggcaaaac ctggggcctc agtgaagatg    60
tcctgcaaga cttctggcta cacctttact agctactgga tgcactgggt aaaacagagg   120
cctggacagg gtctggaatg gattggatac attaatccta ccactggtta tactgactgc   180
aatcagaagt tcaaggacaa ggccacattg actgcagaca gtcctccaa cacagcctac    240
ttgcaactga gcagcctgac atctgaggac tctgcagtct attactgtgc cagatcggct   300
atgtttggta gggggtgggg ccaaggcacc actctcacgg tctcctcagc taaaacgaca   360
cccccatctg tctatccgct ggcccctgga tccgctgccc aaactaactc catggtgacc   420
ctgggatgcc tggtcaaggg ctatttccct gagccagtga cagtgacctg aactctggc    480
tccctgtcca gcggtgtgca ccttccca gctgtcctgc agtctgacct ctacactctg     540
agcagctcag tgactgtccc ctccagcacc tggcccagcg agaccgtcac ctgcaacgtt   600
gcccacccgg ccagcagcac caaggtggac aagaaaattg tgcccaggga ttgtggttgt   660
aagccttgca tatgtacagt cccagaagta tcatctgtct tcatcttccc cccaaagccc   720
aaggatgtgc tcaccattac tctgactcct aaggtcacgt gtgttgtggt agacatcagc   780
aaggatgatc ccgaggtcca gttcagctgg tttgtagatg atgtggaggt gcacacagct   840
cagacgcaac cccgggagga gcagttcaac agcactttcc gctcagtcag tgaacttccc   900
atcatgcacc aggactggct caatggcaag gagttcaaat gcagggtcaa cagtgcagct   960
ttccctgccc ccatcgagaa aaccatctcc aaaaccaaag cagaccgaa ggctccacaa   1020
gtctacacca ttccacctcc caaggagcag atggccaagg ataaagtcag tctgacctgc   1080
atgataacag acttcttccc tgaagacatt actgtggagt ggcagtggaa tgggcagcca   1140
gcggagaact acaagaacac tcagcccatc atggacacag atggctctta cttcgtctac   1200
agcaagctca atgtgcagaa gagcaactgg gaggcaggaa atactttcac ctgctctgtg   1260
ttacatgagg gcctgcacaa ccaccatact gagaagagcc tctcccactc tcctggt     1317
```

<210> SEQ ID NO 15
<211> LENGTH: 219
<212> TYPE: PRT
<213> ORGANISM: Mus musculus

<400> SEQUENCE: 15

```
Asp Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Ser Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
```

-continued

```
               130                 135                 140
Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
                195                 200                 205

Pro Ile Val Lys Ser Phe Asn Arg Asn Glu Cys
    210                 215

<210> SEQ ID NO 16
<211> LENGTH: 657
<212> TYPE: DNA
<213> ORGANISM: Mus musculus

<400> SEQUENCE: 16
gatgttgtga tgacccagac tccactcact ttgtcggtta ccattggaca accagcctcc      60
atctcttgca agtcaagtca gagcctctta catagtgatg aaagacata tttgaattgg      120 ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgtt ggcaaggtac acatttttct     300
cagacgttcg gtggaggctc caagctggaa atcaaacggg ctgatgctgc accaactgta     360
tccatcttcc caccatccag tgagcaattg acatctggag gtgcctcagt cgtgtgcttc     420
ttgaacaact ctacccccaa agacatcaat gtcaagtgga gattgatgg cagtgaacga     480 caaaatggcg tcctgaacag ttggaccgat caggacagca agacagcac ctacagcatg      540 agcagcaccc tcacgttgac caaggacgag tatgaacgac ataacagcta tacctgtgag     600
gccactcaca agacatcaac ttcacccatt gtcaagagct caacaggaa tgagtgt         657
```

ANTI-IDO ANTIBODY AND USES THEREOF

REFERENCE TO SEQUENCE LISTING SUBMITTED ELECTRONICALLY VIA EFS-WEB

The content of the electronically submitted sequence listing in ASCII text file (Name: 191118_SEQT_13179 WOPCT.txt; Size: approximately 20 KB; and Date of Creation: Nov. 18, 2019) filed with the application is herein incorporated by reference in its entirety.

BACKGROUND OF THE DISCLOSURE

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine, leading to immune suppression in the tumor microenvironment. It exists as a 41 kD monomer that is found in several cell populations, including immune cells, endothelial cells, and fibroblasts.

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity may have tremendous therapeutic value. Moreover, inhibitors of IDO can be used to enhance T cell activation when the T cells are suppressed by pregnancy, malignancy, or a virus (e.g., HIV). Although IDO's roles are not as well defined, IDO inhibitors may also find use in the treatment of patients with neurological or neuropsychiatric diseases or disorders (e.g., depression).

Small molecule inhibitors of IDO have been developed to treat or prevent IDO-associated diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO1999/29310). Compounds having IDO inhibitory activity are further reported in WO2004/094409 and WO2016/073770.

The understanding of IDO expression in cancer tissues is limited. Immunohistochemical staining of tissue sections has been shown to be a reliable method of assessing alteration of protein levels in a heterogeneous tissue. Immunohistochemistry (IHC) techniques utilize an antibody to probe and visualize cellular antigens in situ, generally by chromagenic or fluorescent methods. This technique excels because it avoids the unwanted effects of disaggregation and allows for evaluation of individual cells in the context of morphology. In addition, the target protein is not altered by the freezing process. High quality, specific antibodies binding to IDO are needed to detect IDO expression in disease tissues using IHC. Such antibodies may also be used to identify patients who may benefit from treatment with IDO inhibitors.

SUMMARY OF THE DISCLOSURE

One aspect of the present disclosure is directed to an antibody that specifically binds to human Indoleamine 2,3-dioxygenase (IDO), comprising a heavy chain variable region (VH) and a light chain variable region (VL); wherein the VH comprises the VH complementarity determining region (CDR) 1 (VH-CDR1), VH-CDR2, and VH-CDR3 of a VH comprising the amino acid sequence of SEQ ID NO: 4, and the VL comprises the VL-CDR1, VL-CDR2, and VL-CDR3 of a VL comprising the amino acid sequence of SEQ ID NO: 6.

Also provided herein is an antibody that specifically binds to human IDO, comprising a heavy chain variable region (VH) and a light chain variable region (VL); wherein the VH comprises a VH complementarity determining region (CDR) 1 (VH-CDR1), a VH-CDR2, and a VH-CDR3 and the VL comprises a VL-CDR1, a VL-CDR2, and a VL-CDR3; wherein the VH-CDR1 comprises the amino acid sequence set forth in SEQ ID NO:7, the VH-CDR2 comprises the amino acid sequence set forth in SEQ ID NO:8, the VH-CDR3 comprises the amino acid sequence set forth in SEQ ID NO:9, the VL-CDR1 comprises the amino acid sequence set forth in SEQ ID NO:10, the VL-CDR2 comprises the amino acid sequence set forth in SEQ ID NO:11, and the VL-CDR3 comprises the amino acid sequence set forth in SEQ ID NO:12.

Also provided herein is an antibody that specifically binds to human IDO, comprising a heavy chain variable region (VH) and a light chain variable region (VL), wherein the VH comprises the amino acid sequence of SEQ ID NO: 4, and the VL comprises the amino acid sequence set forth in SEQ ID NO: 6.

Also provided herein is an antibody that specifically binds to human IDO, comprising a heavy chain comprising the amino acid sequence set forth in SEQ ID NO: 13 and a light chain comprising the amino acid sequence set forth in SEQ ID NO: 15.

In some embodiments the antibody disclosed herein is a humanized antibody. In some embodiments the antibody disclosed herein is a chimeric antibody, comprising a constant region of a human source.

Also provided herein is a pharmaceutical composition comprising an antibody described herein, and a pharmaceutically acceptable carrier.

Also provided herein is a method of detecting human IDO in a biological sample comprising contacting the biological sample with an antibody described herein under conditions permissive for binding of the antibody to human IDO, and detecting whether a complex is formed between the antibody and human IDO in the biological sample.

Also provided herein is a method of detecting human IDO in a biological sample comprising contacting the biological sample with an antibody described herein under conditions permissive for binding of the antibody to human IDO, and detecting binding of the antibody to human IDO in the biological sample.

Also provided herein is a method of identifying a cancer patient having an IDO-positive cancer, comprising contacting a cancer tissue sample from the patient with an antibody described herein under conditions permissive for binding of the anti-IDO antibody to human IDO, and detecting whether a complex is formed between the anti-IDO antibody and human IDO in the cancer sample.

Also provided herein is a method of identifying a cancer patient having an IDO-positive cancer, comprising contacting a cancer tissue sample from the patient with an antibody described herein under conditions permissive for binding of the anti-IDO antibody to human IDO, and detecting binding of the anti-IDO antibody to human IDO in the cancer sample.

Also provided herein is a method of selecting a cancer patient for treatment with an IDO inhibitor, comprising determining the level of IDO expression in a cancer sample from the patient using immunohistochemistry (IHC), wherein an elevated level of IDO expression indicates that the cancer patient is more likely to benefit from treatment with an IDO inhibitor, wherein IHC is performed using an antibody described herein.

Also provided herein is a method of selecting a cancer patient for treatment with an IDO inhibitor, comprising contacting a cancer sample from the patient with an antibody described herein under conditions permissive for binding of the anti-IDO antibody to human IDO, and detecting whether a complex is formed between the anti-IDO antibody and human IDO in the cancer sample.

Also provided herein is a method of selecting a cancer patient for treatment with an IDO inhibitor, comprising contacting a cancer sample from the patient with an antibody described herein under conditions permissive for binding of the anti-IDO antibody to human IDO, and detecting binding of the anti-IDO antibody to human IDO in the cancer sample.

Also provided herein is a method of treating a cancer patient with an IDO inhibitor comprising a) determining the level of IDO expression in a cancer sample from the patient using immunohistochemistry (IHC) using an anti-IDO antibody described herein, and b) administering to the patient a therapeutically effective amount of the IDO inhibitor.

Also provided herein is a method of treating a cancer patient comprising administering to the patient a therapeutically effective amount of an IDO inhibitor, wherein a cancer sample from the patient has been determined to have an elevated level of IDO expression using immunohistochemistry (IHC), wherein IHC is performed using an anti-IDO antibody described herein.

Also provided herein is a method of treating a cancer patient with an IDO inhibitor comprising determining whether a cancer sample from the patient has an elevated level of IDO expression, as detected by immunohistochemistry (IHC) using an anti-IDO antibody described herein, and administering to the patient a therapeutically effective amount of the IDO inhibitor.

Also provided herein is a method of treating a cancer patient with an IDO inhibitor comprising a) determining the level of IDO expression in a cancer sample from the patient using immunohistochemistry (IHC), wherein an elevated level of IDO expression indicates that the cancer patient is more likely to benefit from treatment with an IDO inhibitor, wherein IHC is performed using an anti-IDO antibody described herein, and b) administering to the patient a therapeutically effective amount of the IDO inhibitor.

Also provided herein is a method of treating a cancer patient with an IDO inhibitor comprising a) contacting a cancer sample from the patient with the anti-IDO antibody described herein under conditions permissive for binding of the anti-IDO antibody to human IDO, b) detecting whether a complex is formed between the anti-IDO antibody and IDO in the cancer sample, and c) administering to the patient a therapeutically effective amount of the IDO inhibitor.

Also provided herein is a method of treating a cancer patient with an IDO inhibitor comprising a) contacting a cancer sample from the patient with the anti-IDO antibody described herein under conditions permissive for binding of the anti-IDO antibody to human IDO, b) detecting binding of the anti-IDO antibody to IDO in the cancer sample, and c) administering to the patient a therapeutically effective amount of the IDO inhibitor.

Other features and advantages of the instant disclosure will be apparent from the following detailed description and examples which should not be construed as limiting. The contents of all cited references, including scientific articles, newspaper reports, GenBank entries, patents and patent applications cited throughout this application are expressly incorporated herein by reference.

BRIEF DESCRIPTION OF THE DRAWINGS/FIGURES

FIG. 1 shows amino acid sequences of the heavy chain and light chain of IDO mAb 1E7. Complementarity Determining Regions (CDRs) determined by Kabat numbering are marked by horizontal lines.

FIG. 2 shows immunohistochemistry staining with anti-IDO mAb 1E7 at 0.05 ug/ml (panels A, B, E, and F) or 0.5 ug/ml (C and D) in cells and tissues. Strong positive staining was observed in vast majority of the HEK293 cells transfected with human IDO (A) and no staining in non-transfected HEK293 cells (B). Strong positive staining was revealed in some H1048 cells (C) and most of the positive staining was absent in cells whose IDO was knocked out by CRISPR ("IDO1 CRISPR Cells") (D). In addition, the positive staining in cervical tumor cells and tumor associated immune cells (E) was blocked by added IDO1 protein (F).

Figure 3:
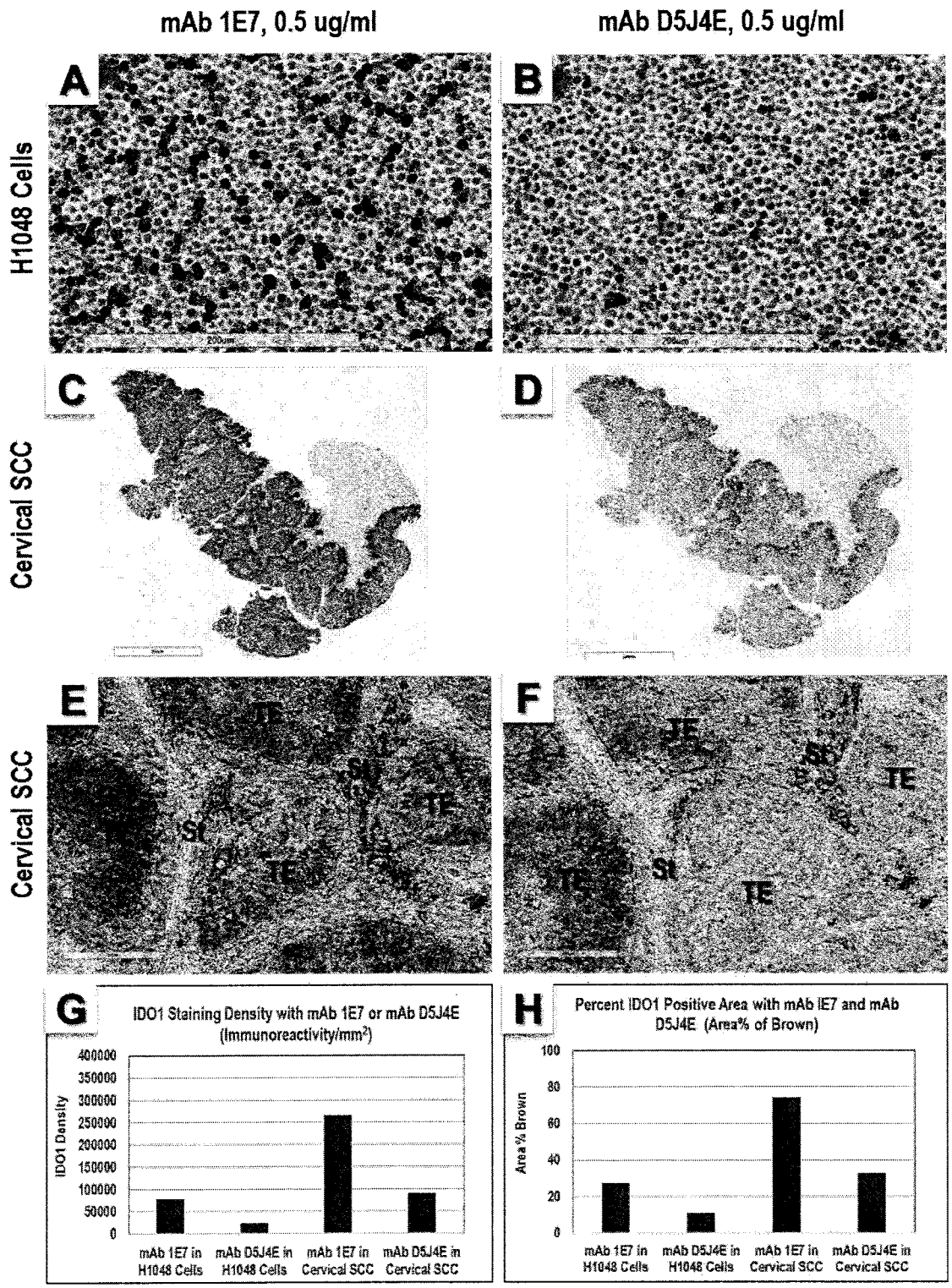

FIG. 3 shows comparison of anti-IDO mAb 1E7 and commercial anti-IDO mAb D5J4E at 0.05 ug/ml in positive control cells and tissues. H1048 is a human lung cancer cell line with low/moderate expression of IDO. The cervical squamous cell carcinoma (SCC) sample used in this test is a high IDO expression tissue verified by RNAscope. Panels C and D are whole slide images. Panels E and F are higher power views. Panels G and H are image analysis of IDO positive staining using HALO software. St, stroma; TE, tumor epithelial cells.

Figure 4:
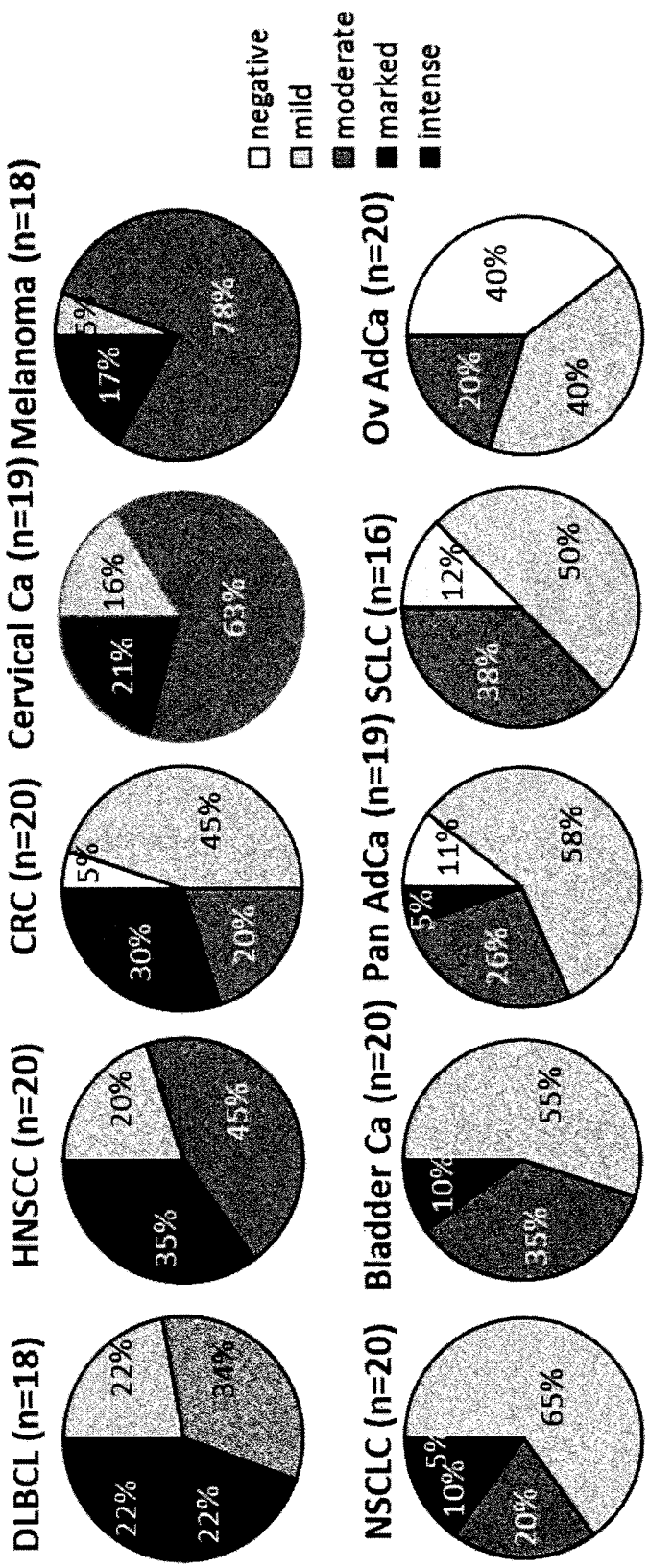

FIG. 4 shows profiling of IDO-positive tumor associated immune cells (TAIC) in 10 tumor types with mAb 1E7. The data is presented as the proportion of samples with different degrees of IDO-positive infiltrates by manual score. The manual score was performed according to the following semi-quantitative scheme: Areas of the digital image corresponding approximately to a field of view on a light microscope at 20× magnification was examined across the whole full-face section. Each sample was designated a score that represented the majority of the tumor (or at least ⅓ of the tumor mass, where significant variability was observed). "Negative," no positive staining or <1 cells per 20× objective field; "mild," 1 to <10 cells per 20× objective field; "moderate," 10 to <50 cells per 20× objective field; "marked," 50 to <200 cells per 20× objective; "intense," >200 cells per 20× objective field.

Figure 5:
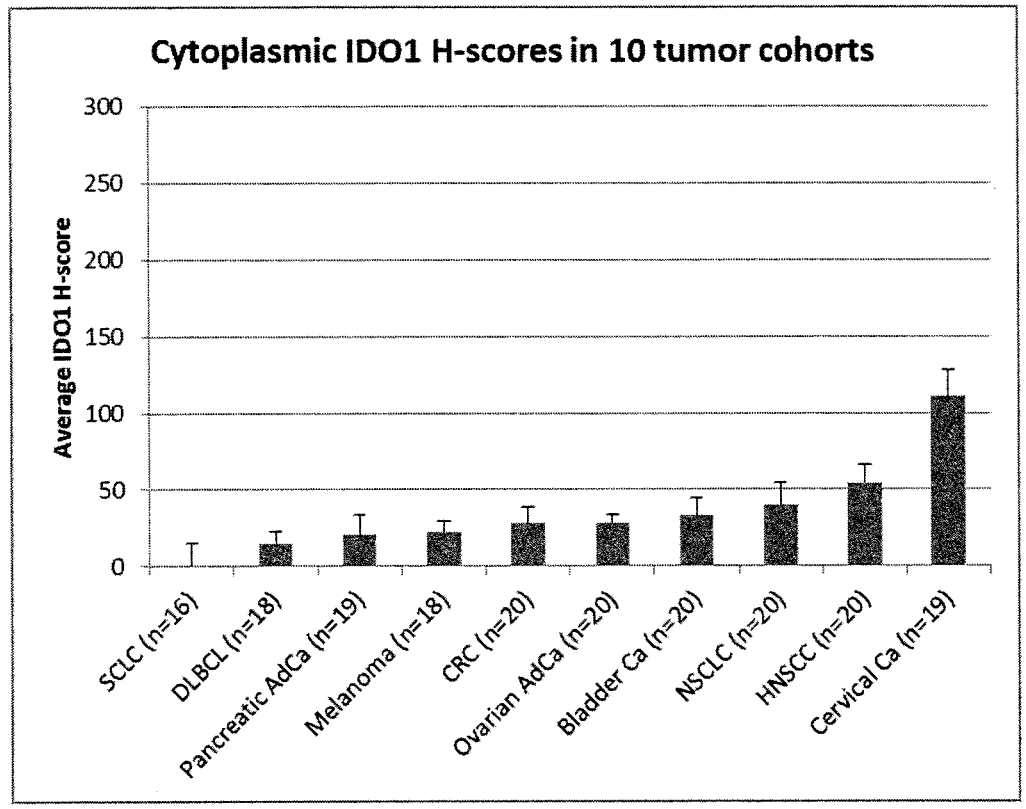

FIG. 5 shows a graphic representation of profiling of IDO-positive tumor cells in 10 tumor types with mAb 1E7. Data is presented as the mean and SEM for cytoplasmic H-score.

DETAILED DESCRIPTION OF DISCLOSURE

The present disclosure relates to antibodies that specifically bind Indoleamine 2,3-dioxygenase (IDO or IDO1, interchangeably herein) ("anti-IDO antibodies"). In some embodiments, the IDO is human IDO. Other aspects of the present disclosure relate to methods of diagnosing and/or treating a subject with IDO-associated conditions. In some embodiments, the anti-IDO antibody may be used to detect IDO expression in the subject. In some embodiments, the subject has a cancer, and the anti-IDO antibody may be used to determine IDO expression level in the subject. In some embodiments, the anti-IDO antibodies are useful for immunocytochemistry (IHC).

I. Terms

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "Indoleamine 2,3-dioxygenase," or "IDO" (also known as IDO1) as used herein includes any variants or isoforms of IDO which are naturally expressed by cells, including but not limited to tumor cells. Accordingly, antibodies described herein may cross-react with IDO from species other than human. Alternatively, the antibodies may be specific for human IDO and do not exhibit any cross-reactivity with other species. IDO or any variants and isoforms thereof, may either be isolated from cells or tissues which naturally express them or be recombinantly produced using well-known techniques in the art and/or those described herein. Human IDO (e.g. NP_002155.1; UniProt ID No. P14902) consists of 403 amino acids.

The term "antibody" refers, in some embodiments, to a protein comprising at least two heavy (H) chains and two light (L) chains inter-connected by disulfide bonds. Each heavy chain is comprised of a heavy chain variable region (abbreviated herein as VH) and a heavy chain constant region (abbreviated herein as CH). In some antibodies, e.g., naturally-occurring IgG antibodies, the heavy chain constant region is comprised of a hinge and three domains, CH1, CH2 and CH3. In some antibodies, e.g., naturally-occurring IgG antibodies, each light chain is comprised of a light chain variable region (abbreviated herein as VL) and a light chain constant region. The light chain constant region is comprised of one domain (abbreviated herein as CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. A heavy chain may have the C-terminal lysine or not. Unless specified otherwise herein, the amino acids in the variable regions are numbered using the Kabat numbering system and those in the constant regions are numbered using the EU system. "Antibody" includes, by way of example, both naturally-occurring and non-naturally-occurring antibodies; monoclonal and polyclonal antibodies; chimeric and humanized antibodies; human and nonhuman antibodies; recombinant antibodies; isolated antibodies; and wholly synthetic antibodies. In some embodiments, the antibodies described herein may be monoclonal antibodies. In some embodiments, the antibodies may be recombinant antibodies. In some embodiments, the antibodies described herein may be isolated antibodies.

Antibodies typically bind specifically to their cognate antigen with high affinity, reflected by a dissociation constant ($K_D$) of $10^{-5}$ to $10^{-11}$M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$M or less, $10^{-8}$ M or less, $5\times10^{-9}$M or less, or between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, at least 95%, at least 97%, or at least 99% sequence identity to the sequence of the given antigen. By way of example, an antibody that binds specifically to human IDO can, in some embodiments, also have cross-reactivity with IDO antigens from certain primate species (e.g., cynomolgus IDO), but cannot cross-react with IDO antigens from other species or with an antigen other than IDO.

An immunoglobulin can be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In some embodiments, the anti-IDO antibodies described herein are of the IgG1 subtype. Immunoglobulins, e.g., IgG1, exist in several allotypes, which differ from each other in at most a few amino acids.

The term "antigen-binding portion" of an antibody, as used herein, refers to one or more fragments of an antibody that retain the ability to specifically bind to an antigen (e.g., human IDO). It has been shown that the antigen-binding function of an antibody can be performed by fragments of a full-length antibody. Examples of binding fragments encompassed within the term "antigen-binding portion" of an antibody, e.g., an anti-IDO antibody described herein, include (i) a Fab fragment (fragment from papain cleavage) or a similar monovalent fragment consisting of the $V_L$, $V_H$, LC and CH1 domains; (ii) a F(ab')2 fragment (fragment from pepsin cleavage) or a similar bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR) and (vii) a combination of two or more isolated CDRs which can optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody," as used herein, refers to an antibody from a population of substantially homogeneous antibodies, i.e., the individual antibodies comprised in the population are substantially similar and bind the same epitope(s) (e.g., the antibodies display a single binding specificity and affinity), except for possible variants that may arise during production of the monoclonal antibody, such variants generally being present in minor amounts. The modifier "monoclonal" indicates the character of the antibody as being obtained from a substantially homogeneous population of antibodies, and is not to be construed as requiring production of the antibody by any particular method.

The term "recombinant antibody," as used herein, includes all antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Such recombinant antibodies comprise variable and constant regions that utilize particular germline immunoglobulin sequences encoded by the germline genes, but include subsequent rearrangements and mutations which occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other proteins and cellular material.

The term "epitope" or "antigenic determinant" refers to a site on an antigen (e.g., IDO) to which an immunoglobulin or antibody specifically binds, e.g., as defined by the specific method used to identify it. Epitopes can be formed both from contiguous amino acids (usually a linear epitope) or non-contiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from an antigen (e.g., from IDO) are tested for reactivity with a given antibody (e.g., anti IDO antibody). Methods of determining spatial conformation of epitopes include techniques in the art and those described herein, for example, X-ray crystallography, X-ray co-crystallography, antigen mutational analysis, 2-dimensional nuclear magnetic resonance and HDX-MS (see, e.g., Epitope Mapping Protocols in Methods in Molecular Biology, Vol. 66, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope on IDO" with the antibodies described herein include, for example, epitope mapping methods, such as, X-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments, e.g., BIACORE® surface plasmon resonance (SPR) analysis. In some embodiments, an antibody competes with, and inhibits binding of another antibody to a target by at least 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include: competition for binding to cells expressing IDO, e.g., by flow cytometry, such as described in the Examples. Other methods include: SPR (e.g., BIACORE®), solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 instrument using the predetermined antigen, e.g., recombinant human IDO, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. Available methods for determining the $K_D$ of an antibody include surface plasmon resonance, a biosensor system such as a BIACORE® system or flow cytometry and Scatchard analysis.

The term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some embodiments, a predicted nonessential amino acid residue in an anti-IDO antibody is replaced with another amino acid residue from the same side chain family Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS*, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the BLASTN, BLASTX and BLASTP programs (version 2.0) of Altschul, et al. (1990) *J. Mol. Biol.* 215:403-10. BLAST nucleotide searches can be performed with the BLASTN program, score=100, word length=12 to obtain nucleotide sequences homologous to the nucleic acid molecules described herein. BLAST protein searches can be performed with the BLASTX program, score=50, word length=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., BLASTX, BLASTP, and BLASTN) can be used. See www.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, the term "elevated level of IDO expression" or "elevated IDO level" refers to an increase in IDO RNA or protein level, for example, an increase in IDO protein level in a cell or a tissue sample, such as a biological sample from a cancer patient, e.g., cancer tissue sample, as compared to a control tissue sample, such as a biological sample from a subject who does not have the cancer, e.g., a healthy or normal subject. The increase may be at least about 10%, at least about 20%, at least about 30%, at least about 40%, at least about 50%, at least about 60%, at least about 70%, at least about 80%, at least about 90%, at least about 100%, or at least 200%. In some embodiments, the increase may range from about 10% to about 80%, from 30% to about 80%, from 40% to about 80%, from about 10% to about 60%, from 30% to about 60%, from 40% to about 60%. In some embodiments, the IDO expression level in a subject such as a cancer patient, as compared to a control or a normal subject, may be at least about 20% higher. In some embodiments, the IDO expression level in a subject such as a cancer patient, as compared to a control or a normal subject, may be at least about 30% higher. In some embodiments, the IDO expression level in a subject such as a cancer patient, as compared to a control or a normal subject, may be at least about 40% higher. In some embodiments, the IDO expression level in a subject such as a cancer patient, as compared to a control or a normal subject, may be at least about 50% higher. In some embodiments, the IDO expression level in a subject such as a cancer patient, as compared to a control or a normal subject, may be at least about 60% higher. In some embodiments, the IDO expression level in a subject such as a cancer patient, as compared to a control or a normal subject, may be at least about 70% higher. In some embodiments, the IDO expression level in a subject such as a cancer patient, as compared to a control or a normal subject, may be at least about 80% higher. In some embodiments, the IDO expression level in a subject such as a cancer patient, as compared to a control or a normal subject, may be at least about 90% higher. The IDO expression level may be determined by an antibody-based method, for example, IHC, or FACS, using the antibody described herein, by any other method known in the art, including those used to detect protein or DNA expression.

As used herein, the terms "IDO inhibitor", "IDO blocker" and terms similar thereto refer to agents capable of inhibiting the activity of IDO, thereby reversing IDO-mediated immunosuppression. An IDO inhibitor may be a competitive, noncompetitive, or irreversible IDO inhibitor. "A competitive IDO inhibitor" is a compound that reversibly inhibits IDO enzyme activity at the catalytic site; "a noncompetitive IDO Inhibitor" is a compound that reversibly inhibits IDO enzyme activity at a non-catalytic site; and "an irreversible IDO inhibitor" is a compound that irreversibly eliminates IDO enzyme activity by forming a covalent bond (or other stable means of inhibiting enzyme function) with the enzyme. Exemplary the IDO inhibitors include 1-methyl-DL-tryptophan; p-(3-benzofuranyl)-DL-alanine; p-[3 benzo(b)thienyl]-DL-alanine; and 6-nitro-L-tryptophan (WO 99/29310). Compounds having IDO inhibitory activity are further reported in WO 2004/094409. BMS-986205 is another small molecule IDO inhibitor.

As used herein, "administering" refers to the physical introduction of a composition comprising a therapeutic agent to a subject, using any of the various methods and delivery systems known to those skilled in the art. Different routes of administration for the anti-IDO antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion).

As used herein, "cancer" refers a broad group of diseases characterized by the uncontrolled growth of abnormal cells in the body. Unregulated cell division can result in the formation of malignant tumors or cells that invade neighboring tissues and can metastasize to distant parts of the body through the lymphatic system or bloodstream.

The term "IDO-positive cancer" refers to a cancer comprising cells that express IDO. In some embodiments, expression of IDO mRNA is determined by a method selected from in situ hybridization and RT-PCR (including quantitative RT-PCR). Alternatively, expression of IDO can be determined, for example, using antibodies that bind to IDO in a method such as immunohistochemistry, FACS, etc.

The term "IDO-positive cancer cell" refers to a cancer cell that expresses IDO.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition, or biochemical indicia associated with a disease or enhancing overall survival. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, an increase in overall survival (the length of time from either the date of diagnosis or the start of treatment for a disease, such as cancer, that the patient diagnosed with the disease is still alive), or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that promotes cancer regression in a subject. In some embodiments, a therapeutically effective amount of the drug promotes cancer regression to the point of eliminating the cancer. "Promoting cancer regression" means that administering an effective amount of the drug, alone or in combination with an antineoplastic agent, results in a reduction in tumor growth or size, necrosis of the tumor, a decrease in severity of at least one disease symptom, an increase in frequency and duration of disease symptom-free periods, an increase in overall survival, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug inhibits cell growth or tumor growth by at least about 20%, by at least about 40%, by at least about 60%, or by at least about 80% relative to untreated subjects. In some embodiments, a therapeutically effective amount or dosage of the drug completely inhibits cell growth or tumor growth, i.e., inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In some embodiments described herein, tumor regression can be observed and continue for a period of at least about 20 days, at least about 40 days, or at least about 60 days.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

As used herein, the terms "ug" and "uM" are used interchangeably with "μg" and "μM," respectively.

Various aspects described herein are described in further detail in the following subsections.

Described herein are antibodies which are capable of specifically binding to human IDO. In some embodiments, the antibodies specifically bind to IDO, thereby allowing determination of IDO expression level in a biological sample from a patient. In some embodiments the IDO expression level is determined by immunohistochemistry (IHC).

In some embodiments, the anti-IDO antibodies described herein bind to human IDO with high affinity, for example, with a $K_D$ of $10^{-6}$ M or less, $10^{-7}$ M or less, $10^{-8}$ M or less, $10^{-9}$M or less, $10^{-10}$ M or less, $10^{-11}$M or less, $10^{-12}$ M or less, $10^{-12}$ M to $10^{-7}$ M, $10^{-11}$M to $10^{-7}$ M, $10^{-10}$ M to $10^{-7}$ M, or $10^{-9}$M to $10^{-7}$ M, e.g., as determined by Surface Plasmon Resonance, e.g. using BIACORE™, or e.g., as determined by ELISA, e.g., an IDO ELISA kit, e.g., ABCAM ab100592. In some embodiments, the antibodies bind to human IDO with an $EC_{50}$ of 100 nM or less, 10 nM or less, 1 nM or less. In some embodiments, the anti-IDO antibody specifically binds human IDO with an association constant ($k_a$) rate of at least about $1\times10^3$ ms$^{-1}$, at least about $5\times10^3$ ms$^{-1}$, at least about $1\times10^4$ ms$^{-1}$, at least about $5\times10^4$ ms$^{-1}$, at least about $1\times10^5$ ms$^{-1}$, at least about $5\times10^5$ ms$^{-1}$, or at least about $1\times10^6$ ms$^{-1}$, wherein $k_a$ is measured by surface plasmon resonance (Biacore) analysis. In some embodiments, the anti-IDO antibody specifically binds human IDO with a dissociation constant ($k_d$) rate of about 0.1 s$^{-1}$ or less, 0.05 s$^{-1}$ or less, 0.01 s$^{-1}$ or less, $5\times10^{-3}$ s$^{-1}$ or less, $1\times10^{-3}$ s$^{-1}$ or less, $5\times10$'s$^{-1}$ or less, $1\times10$'s$^{-1}$ or less, $5\times10^{-5}$ s$^{-1}$ or less, or $1\times10^{-5}$ s$^{-1}$ or less, wherein $K_D$ is measured by surface plasmon resonance (Biacore) analysis.

In some embodiments, the antibody that specifically binds to human IDO comprises a heavy chain variable region (VH) and a light chain variable region (VL); wherein the VH comprises the VH complementarity determining region (CDR) 1 (VH-CDR1), VH-CDR2, and VH-CDR3 of a VH comprising the amino acid sequence of SEQ ID NO: 4, and the VL comprises the VL-CDR1, VL-CDR2, and VL-CDR3 of a VL comprising the amino acid sequence of SEQ ID NO: 6.

In some embodiments, the antibody specifically binds to IDO comprises a heavy chain variable region (VH) and a light chain variable region (VL); wherein the VH comprises a VH complementarity determining region (CDR) 1, a VH-CDR2, and a VH-CDR3 and the VL comprises a VL-CDR1, a VL-CDR2, and a VL-CDR3; wherein the VH-CDR1 comprises the amino acid sequence set forth in SEQ ID NO:7, the VH-CDR2 comprises the amino acid sequence set forth in SEQ ID NO:8, the VH-CDR3 comprises the amino acid sequence set forth in SEQ ID NO:9, the VL-CDR1 comprises the amino acid sequence set forth in SEQ ID NO:10, the VL-CDR2 comprises the amino acid sequence set forth in SEQ ID NO:11, and the VL-CDR3 comprises the amino acid sequence set forth in SEQ ID NO:12.

In some embodiments, the antibody that specifically binds to human IDO comprises a heavy chain variable region (VH) and a light chain variable region (VL); wherein the VH comprises an amino acid sequence having at least about 70%, at least about 80%, at least about 90%, at least about 95%, at least about 96%, at least about 97%, at least about 98%, or at least about 99% sequence identity to the amino acid sequence set forth in SEQ ID NO: 4. In some embodiments, the VH comprises an amino acid sequence having at least about 95% sequence identity to the amino acid sequence set forth in SEQ ID NO: 4. In some embodiments, the VH comprises an amino acid sequence having at least about 98% sequence identity to the amino acid sequence set forth in SEQ ID NO: 4. In some embodiments, the VH comprises an amino acid sequence having at least about 99% sequence identity to the amino acid sequence set forth in SEQ ID NO: 4. In some embodiments, the VH comprises the amino acid sequence set forth in SEQ ID NO: 4.

In some embodiments, the VL comprises an amino acid sequence having at least about 70%, at least about 80%, at least about 90%, at least about 95%, at least about 96%, at least about 97%, at least about 98%, or at least about 99% sequence identity to the amino acid sequence set forth in SEQ ID NO: 6. In some embodiments, the VL comprises an amino acid sequence having at least about 95% sequence identity to the amino acid sequence set forth in SEQ ID NO: 6. In some embodiments, the VL comprises an amino acid sequence having at least about 98% sequence identity to the amino acid sequence set forth in SEQ ID NO: 6. In some embodiments, the VL comprises an amino acid sequence having at least about 99% sequence identity to the amino acid sequence set forth in SEQ ID NO: 6. In some embodiments, the VL comprises the amino acid sequence set forth in SEQ ID NO: 6.

In some embodiments, the antibody that specifically binds to human IDO comprises a heavy chain variable region (VH) and a light chain variable region (VL), wherein the VH comprises the amino acid sequence of SEQ ID NO: 4, and the VL comprises the amino acid sequence set forth in SEQ ID NO: 6.

In some embodiments, the antibody cross competes for binding to human IDO with an antibody comprising a VH comprising the amino acid sequence set forth in SEQ ID NO: 4 and a VL comprising the amino acid sequence set forth in SEQ ID NO: 6. In some embodiments, the antibody binds to the same epitope as an antibody comprising a VH comprising the amino acid sequence set forth in SEQ ID NO: 4 and a VL comprising the amino acid sequence set forth in SEQ ID NO: 6.

In some embodiments, the antibody comprises a heavy chain comprising an amino acid sequence having at least about 70%, at least about 80%, at least about 85%, at least about 90%, at least about 95%, at least about 96%, at least about 97%, at least about 98%, or at least about 99% sequence identity to the amino acid sequence set forth in SEQ ID NO: 13. In some embodiments, the heavy chain comprises an amino acid sequence having at least about 95% sequence identity to the amino acid sequence set forth in SEQ ID NO: 13. In some embodiments, the heavy chain comprises an amino acid sequence having at least about 98% sequence identity to the amino acid sequence set forth in SEQ ID NO: 13. In some embodiments, the heavy chain comprises an amino acid sequence having at least about 99% sequence identity to the amino acid sequence set forth in SEQ ID NO: 13. In some embodiments, the heavy chain comprises the amino acid sequence set forth in SEQ ID NO: 13.

In some embodiments, the antibody comprises a light chain comprising an amino acid sequence having at least about 70%, at least about 80%, at least about 85%, at least about 90%, at least about 95%, at least about 96%, at least about 97%, at least about 98%, or at least about 99% sequence identity to the amino acid sequence set forth in SEQ ID NO: 15. In some embodiments, the light chain comprises an amino acid sequence having at least about 95% sequence identity to the amino acid sequence set forth in SEQ ID NO: 15. In some embodiments, the light chain comprises an amino acid sequence having at least about 98% sequence identity to the amino acid sequence set forth in SEQ ID NO: 15. In some embodiments, the light chain comprises an amino acid sequence having at least about 99% sequence identity to the amino acid sequence set forth in SEQ ID NO: 15. In some embodiments, the light chain comprises the amino acid sequence set forth in SEQ ID NO: 15.

In some embodiments, the antibody that specifically binds to human IDO comprises a heavy chain comprising the amino acid sequence set forth in SEQ ID NO: 13 and a light chain comprising the amino acid sequence set forth in SEQ ID NO: 15.

In some embodiments, the antibody cross competes for binding to human IDO with an antibody comprising a heavy chain comprising the amino acid sequence set forth in SEQ ID NO: 13 and a light chain comprising the amino acid sequence set forth in SEQ ID NO: 15. In some embodiments, the antibody binds the same epitope as an antibody comprising a heavy chain comprising the amino acid sequence set forth in SEQ ID NO: 13 and a light chain comprising the amino acid sequence set forth in SEQ ID NO: 15.

The above exemplary amino acid sequences can further include a signal peptide. The signal peptide can be an immunoglobulin signal peptide or a heterologous signal peptide (i.e., a signal peptide from a non-immunoglobulin protein).

In some embodiments, heavy and light chains of anti-IDO antibodies can be expressed with the respective signal sequence that was linked to each chain in the hybridoma from which they were cloned.

In some embodiments, the heavy and light chains of the anti-IDO antibody (e.g., 1E7) can be engineered with signal sequences that differ from those present in the hybridomas from which they were cloned.

In some embodiments, the antibody described herein is capable of specifically staining IDO in a cell by immunohistochemistry (IHC). In some embodiments, the antibody described herein is capable of specifically staining IDO in a biological sample by immunohistochemistry (IHC). In some embodiments, the antibody is capable of specifically staining IDO in a cancer tissue sample by immunohistochemistry (IHC). In some embodiments, the antibody is capable of specifically staining IDO in a formalin fixed cancer tissue sample by IHC. In some embodiments, the antibody is capable of specifically staining IDO in a formalin fixed paraffin embedded (FFPE) cancer tissue sample by IHC.

In some embodiments, the anti-IDO antibody described herein may be a humanized antibody. In some embodiments, the anti-IDO antibody described herein may be a chimeric antibody. In some embodiments, the anti-IDO antibody described herein may be a chimeric antibody comprising a constant region of a human source. In some embodiments, the anti-IDO antibody described herein may be a bispecific antibody.

In some embodiments, the antibody may be an IgG1, an IgG2, an IgG3, an IgG4 or a variant thereof. In some embodiments, the antibody may be an IgG1, an IgG2a, an IgG2b, an IgG3 or a variant thereof. In some embodiments, the antibody may be an IgG1 antibody.

A VH domain, or one or more CDRs thereof, described herein can be linked to a constant domain for forming a heavy chain, e.g., a full length heavy chain. Similarly, a VL domain, or one or more CDRs thereof, described herein can be linked to a constant domain for forming a light chain, e.g., a full length light chain. A full length heavy chain (optionally with the exception of the C-terminal lysine (K) or with the exception of the C-terminal glycine and lysine (GK), which can be absent) and full length light chain may combine to form a full length antibody.

In some embodiments, an anti-IDO antibody comprises a heavy chain variable region from a particular germline heavy chain immunoglobulin gene and/or a light chain variable region from a particular germline light chain immunoglobulin gene.

Anti-IDO antibodies described herein can comprise a heavy chain variable region comprising CDR1, CDR2 and CDR3 sequences and a light chain variable region comprising CDR1, CDR2 and CDR3 sequences, wherein one or more of these CDR sequences comprise specified amino acid sequences described herein, or conservative modifications thereof, and wherein the antibodies retain the desired functional properties of the anti-IDO antibodies described herein.

Conservative modifications, such as amino acid substitutions, can be made in portions of the antibodies other than, or in addition to, the CDRs. For example, conservative amino acid modifications can be made in a framework region or in the Fc region. A variable region or a heavy or light chain can comprise 1, 2, 3, 4, 5, 6, 7, 8, 9, 10, 1-2, 1-3, 1-4, 1-5, 1-10, 1-15, 1-20, 1-25, or 1-50 conservative amino acid substitutions relative to the anti-IDO sequences provided herein. In some embodiments, an anti-IDO antibody comprises a combination of conservative and non-conservative amino acid modification.

Also provided are engineered and modified antibodies that can be prepared using an antibody having one or more of the VH and/or VL sequences disclosed herein as starting material to engineer a modified antibody, which modified antibody can have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

In some embodiments, the framework sequences for use in the anti-IDO antibodies described herein are those that are structurally similar to the framework sequences used by the anti-IDO antibodies described herein. The VH CDR1, CDR2 and CDR3 sequences, and the VL CDR1, CDR2 and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see, e.g., U.S. Pat. Nos. 5,530,101; 5,585,089; 5,693,762; and 6,180,370 to Queen et al.).

Engineered anti-IDO antibodies described herein include those in which modifications have been made to framework residues within VH and/or VL, or to the constant regions, e.g., to improve the properties of the antibody. For example, such modifications may be made to decrease the immunogenicity of the antibody, to improve one or more binding properties (e.g., affinity) of the antibody, to reduce potential chemical degradation, increase potency of the antibody, to remove deamidation sites, to increase biological half-life, to increase solubility, to change glycosylation, or to alter one or more functional properties of the antibody.

Generally, variable regions described herein can be linked to an Fc comprising one or more modification, typically to alter one or more functional properties of the antibody, such as serum half-life, complement fixation, Fc receptor binding, antigen-dependent cellular cytotoxicity, and/or antibody-dependent cellular phagocytosis. Furthermore, an antibody described herein can be chemically modified (e.g., one or more chemical moieties can be attached to the antibody) or be modified to alter its glycosylation, to alter one or more functional properties of the antibody.

In some embodiments, the antibodies described herein have higher stability than a reference antibody. In some embodiments, the antibodies described herein have a higher melting temperature than a reference antibody. In some embodiments, the antibodies described herein have a lower tendency for aggregation than a reference antibody. In some embodiments, the antibodies described herein have a higher solubility than a reference antibody. In some embodiments, the antibodies described herein have a higher rate of absorption, lower toxicity, higher biological activity and/or target selectivity, better manufacturability, and/or lower immunogenicity than a reference antibody. The reference antibody can be another antibody or fragments thereof, or conjugate thereof, that binds to IDO.

Also provided herein are polynucleotide or a set of polynucleotides encoding the antibody described herein.

Also provided herein are vector or a set of vectors comprising the polynucleotide or the set of polynucleotides described herein.

Also provided herein are host cells comprising the antibody described herein, the polynucleotide or the set of polynucleotides described herein, or the vector or the set of vectors described herein. In some embodiments, the host cells are CHO cells. In some embodiments, the host cells are CHO cells. In some embodiments, the host cells are HEK293 cells.

In some embodiments, the nucleic acids that encode the anti-IDO antibodies described herein can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In some embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Some nucleic acids molecules described herein are those encoding the VH and VL sequences of the anti-IDO antibodies. Exemplary DNA sequence encoding the VH and VL sequences of 1E7 are set forth in SEQ ID NOs: 3 and 5, respectively. Exemplary DNA sequence encoding the heavy chain and light chain sequences of 1E7 are set forth in SEQ ID NOs: 14 and 16, respectively. The exemplary nucleic acid sequences described herein can further include sequences encoding a signal peptide sequence. The nucleic acid molecules described herein may be modified to delete specific sequences, e.g., restriction enzyme recognition sequences, or to optimize codons.

Also provided herein are methods of producing an antibody comprising culturing the host cell of described herein so that the antibody is produced. A method for making anti-IDO antibodies can comprise expressing the heavy chain and the light chains in a cell line comprising the nucleotide sequence(s) encoding the VH and VL sequences, e.g., for 1E7, of SEQ ID NOs: 3 and 5, respectively, or comprising the nucleotide sequences encoding the heavy and light chains, e.g., for 1E7, of SEQ ID Nos: 14 and 16, respectively. A method for making 1E7 can comprise expressing the heavy chain and the light chains in a cell line comprising the nucleotide sequences encoding the heavy and light chains with a signal peptide.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2, and/or CH3). The sequences of human and mouse heavy chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human and mouse light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see, e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Also provided herein are nucleic acid molecules encoding VH and VL sequences that are homologous to those of the anti-IDO antibodies described herein. Exemplary nucleic acid molecules encode VH and VL sequences that are at least 70% identical, for example, at least 75%, at least 80%, at least 85%, at least 90%, at least 95%, or at least 99% identical, to nucleic acid molecules encoding the VH and VL sequences of the anti-IDO antibodies. Also provided herein are nucleic acid molecules with conservative substitutions (i.e., substitutions that do not alter the resulting amino acid sequence upon translation of nucleic acid molecule), e.g., for codon optimization.

Chimeric or humanized anti-IDO antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see, e.g., U.S. Pat. No. 4,816,567 to Cabilly et al.). To create a humanized antibody, the murine CDR regions can be inserted into a human framework using methods known in the art (see, e.g., U.S. Pat. No. 5,225,539 to Winter, and U.S. Pat. Nos. 5,530,101; 5,585,089; 5,693,762 and 6,180,370 to Queen et al).

Additionally or alternatively, the recombinant expression vector described herein can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In some embodiments, the heavy and light chains of the anti-IDO antibody (e.g., 1E7) can be engineered with signal sequences that differ from those present in the hybridomas from which they were cloned. In addition to the antibody chain genes, recombinant expression vectors can carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, CA (1990)). It will be appreciated by those skilled in the art that the design of the expression vector, including the selection of regulatory sequences, can depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g, U.S. Pat. Nos. 4,399,216, 4,634,665 and 5,179,017, all by Axel et al). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like.

It is possible to express the anti-IDO antibodies described herein in either prokaryotic or eukaryotic host cells, such as mammalian cells. Certain mammalian host cells for expressing the recombinant anti-IDO antibodies described herein include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R J. Kaufman and P. A. Sharp (1982) Mol. Biol. 759:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Also provided herein are pharmaceutical compositions comprising the antibody described herein and a pharmaceutically acceptable carrier.

Anti-IDO antibodies described herein may be used for diagnostic purposes, including sample testing, immunohistochemistry and in vivo imaging.

Provided herein are immunoconjugates comprising the antibody described herein and an agent. In some embodiments, the agent may be selected from the group consisting of a label, a cytotoxic agent, an imaging agent (e.g. a fluorescent label), a radioisotope, a second antibody, an enzyme, and any combination thereof. In some embodiments the moiety attached to an anti-IDO antibody is selected from the group consisting of a binding moiety, a labeling moiety, and a biologically active moiety. In some embodiments, the agent may be a label. In some embodiments, the agent may be an imaging agent. In some embodiments, the agent may be a second antibody. In some embodiments, the agent may be a cytotoxic agent. In some embodiments, the agent is selected from the group consisting of a cytotoxin, a non-cytotoxic drug, a radioactive agent, a second antibody, an enzyme, an anti-neoplastic agent, and any combination thereof. Anti-IDO antibodies described herein can also be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. In some embodiments, the linker comprises a peptidyl linker such as Val-Cit, Ala-Val, Val-Ala-Val, Lys-Lys, Pro-Val-Gly, Val-Gly-Val, Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295. In some embodiments, conjugation methods result in linkages which are substantially (or nearly) non-immunogenic, e.g., peptide- (i.e., amide-), sulfide-, (sterically hindered), disulfide-, hydrazone-, and ether linkages. These linkages are nearly non-immunogenic and show reasonable stability within serum (see e.g., Senter, P. D., Curr. Opin. Chem. Biol. 13 (2009) 235-244; WO 2009/059278; WO 95/17886).

Also provided herein are methods of detecting human IDO in a biological sample comprising contacting the biological sample with the antibody described herein under conditions permissive for binding of the antibody to human IDO, and detecting whether a complex is formed between the antibody and human IDO in the biological sample. Also provided herein are methods of detecting human IDO in a biological sample comprising contacting the biological sample with the antibody described herein under conditions permissive for binding of the antibody to human IDO, and detecting binding of the antibody to human IDO in the biological sample.

In some embodiments, the biological sample may be a cancer sample, such as a cancer tissue sample. The term "tissue sample" refers to a collection of similar cells obtained from a tissue of a subject or patient, e.g., a tissue containing nucleated cells with chromosomal material. In some embodiments, the biological sample may be a formaldehyde-fixed tissue sample, e.g., from a cancer patient. In some embodiments, the biological sample may be Formalin Fixed Paraffin Embedded (FFPE) tissue sample, e.g., from a cancer patient.

In some embodiments, the biological sample may be a sample of diffuse large B-cell lymphoma (DLBCL), head and neck squamous cell carcinoma (HNSCC), cervical carcinoma, melanoma, colorectal carcinoma (CRC), non small-cell lung carcinoma (NSCLC), bladder carcinoma, pancreatic adenocarcinoma, small cell lung cancer (SCLC), or ovarian adenocarcinoma.

In some embodiments, the biological sample may be a blood sample. In some embodiments, the biological may be derived from a blood sample, such as plasma, serum, and/or blood cells (e.g., white blood cells).

Also provided herein are methods of identifying a cancer patient having an IDO-positive cancer, comprising contacting a cancer sample from the patient with the anti-IDO antibody described herein under conditions permissive for binding of the anti-IDO antibody to human IDO, and detecting whether a complex is formed between the anti-IDO antibody and human IDO in the cancer sample. Also provided herein are methods of identifying a cancer patient having a IDO-positive cancer, comprising contacting a cancer sample from the patient with the anti-IDO antibody described herein under conditions permissive for binding of the anti-IDO antibody to human IDO, and detecting binding of the anti-IDO antibody to human IDO in the cancer sample. In some embodiments, the methods may use IHC.

Also provided herein are methods of selecting a cancer patient for treatment with an IDO inhibitor, comprising determining the level of IDO expression in a cancer sample from the patient using immunohistochemistry (IHC), wherein an elevated level of IDO expression indicates that the cancer patient is more likely to benefit from treatment with an IDO inhibitor, wherein IHC is performed using the antibody described herein.

Also provided herein are methods of selecting a cancer patient for treatment with an IDO inhibitor, comprising contacting a cancer sample from the patient with the anti-IDO antibody described herein under conditions permissive for binding of the anti-IDO antibody to human IDO, and detecting whether a complex is formed between the anti-IDO antibody and human IDO in the cancer sample. Also provided herein are methods of selecting a cancer patient for treatment with an IDO inhibitor, comprising contacting a cancer sample from the patient with the anti-IDO antibody described herein under conditions permissive for binding of the anti-IDO antibody to human IDO, and detecting binding of the anti-IDO antibody to human IDO in the cancer sample. In some embodiments, the methods may use IHC.

Also provided herein are methods of treating a cancer patient comprising administering to the patient a therapeutically effective amount of an IDO inhibitor, wherein a cancer sample from the patient has been determined to have an elevated level of IDO expression as detected by immunohistochemistry (IHC), wherein IHC is performed using the antibody described herein.

Also provided herein are methods of treating a cancer patient with an IDO inhibitor comprising (a) determining whether a cancer patient has an IDO-positive cancer as detected by immunohistochemistry (IHC) using the antibody described herein, and (b) administering to the patient a therapeutically effective amount of the IDO inhibitor.

Also provided herein are methods of treating a cancer patient with an IDO inhibitor comprising determining whether a cancer sample from the patient has an elevated level of IDO expression, as detected by immunohistochemistry (IHC) using the antibody described herein, and administering to the patient a therapeutically effective amount of the IDO inhibitor.

Also provided herein are methods of treating a cancer patient with an IDO inhibitor comprising: a) determining the level of IDO expression in a cancer sample from the patient using immunohistochemistry (IHC) using the antibody described herein, and b) administering to the patient a therapeutically effective amount of the IDO inhibitor.

Also provided herein are methods of treating a cancer patient with an IDO inhibitor comprising: a) determining the level of IDO expression in a cancer sample from the patient using immunohistochemistry (IHC), wherein an elevated level of IDO expression indicates that the cancer patient is more likely to benefit from treatment with an IDO inhibitor, wherein IHC is performed using the antibody described herein, and b) administering to the patient a therapeutically effective amount of the IDO inhibitor.

Also provided herein are methods of treating a cancer patient with an IDO inhibitor comprising: a) contacting a cancer sample from the patient with the anti-IDO antibody described herein under conditions permissive for binding of the anti-IDO antibody to human IDO, b) detecting whether a complex is formed between the anti-IDO antibody and human IDO in the cancer sample, and c) administering to the patient a therapeutically effective amount of the IDO inhibitor. Also provided herein are methods of treating a cancer patient with an IDO inhibitor comprising: a) contacting a cancer sample from the patient with the anti-IDO antibody described herein under conditions permissive for binding of the anti-IDO antibody to human IDO, b) detecting binding of the anti-IDO antibody to human IDO in the cancer sample, and c) administering to the patient a therapeutically effective amount of the IDO inhibitor. In some embodiments, binding of the anti-IDO antibody to human IDO may be detected by IHC.

In some embodiments, the method increases the objective response rate of the subject. In certain embodiments, the method induces a complete response in the subject. In some embodiments, the method induces a partial response in the subject.

The antibodies disclosed herein may also be used as therapeutic agents for treating cancer. Also provided herein are methods of treating cancer comprising administering the antibody to a subject in need thereof. In some embodiments, the antibody may be a humanized antibody comprising a heavy chain variable region (VH) and a light chain variable region (VL); wherein the VH comprises a VH complementarity determining region (CDR) 1, a VH-CDR2, and a VH-CDR3 and the VL comprises a VL-CDR1, a VL-CDR2, and a VL-CDR3; wherein the VH-CDR1 comprises the amino acid sequence set forth in SEQ ID NO:7, the VH-CDR2 comprises the amino acid sequence set forth in SEQ ID NO:8, the VH-CDR3 comprises the amino acid sequence set forth in SEQ ID NO:9, the VL-CDR1 comprises the amino acid sequence set forth in SEQ ID NO:10, the VL-CDR2 comprises the amino acid sequence set forth in SEQ ID NO:11, and the VL-CDR3 comprises the amino acid sequence set forth in SEQ ID NO:12. In some embodiments, the antibody may be a chimeric antibody. In some embodiments, the antibody may be an immunoconjugate, e.g., an antibody-drug conjugate. In some embodiments, the method of treating cancer further comprises administering another therapeutic agent, e.g., a chemotherapeutic agent or another protein agent, to the subject.

Cancers whose growth can be inhibited using the methods of the disclosure include cancers typically responsive to immunotherapy and those that are not typically responsive to immunotherapy. Cancers that can be treated include IDO positive cancers. Cancers can be cancers with solid tumors or hematolotical malignancies (liquid tumors). Non-limiting examples of cancers for treatment include squamous cell carcinoma, small-cell lung cancer, non-small cell lung cancer, squamous non-small cell lung cancer (NSCLC), non-squamous NSCLC, glioma, gastrointestinal cancer, renal cancer (e.g., clear cell carcinoma), ovarian cancer, liver cancer, colorectal cancer, endometrial cancer, kidney cancer (e.g., renal cell carcinoma (RCC)), prostate cancer (e.g., hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, rectal cancer, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, environmentally-induced cancers including those induced by asbestos, virus-related cancers or cancers of viral origin (e.g., human papilloma virus (HPV-related or -originating tumors)); and any combinations of said cancers.

Non-limiting examples of cancers for treatment include hematological malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) of the T-cell type; a/d T-NHL hepatosplenic lymphoma; peripheral/post-thymic T cell lymphoma (pleomorphic and immunoblastic subtypes); angiocentric (nasal) T-cell lymphoma; and any combinations of said cancers.

The methods described herein can also be used for treatment of metastatic cancers, unresectable, refractory cancers (e.g., cancers refractory to previous immunotherapy, e.g., with a blocking CTLA-4 or PD-1 antibody), and/or recurrent cancers.

In some embodiments, the subject has a cancer selected from non-small cell lung cancer (NSCLC), head and neck squamous cell carcinoma (HNSCC), melanoma, bladder cancer, pancreatic cancer, gastric cancer, colon cancer, renal cell carcinoma (RCC), small-cell lung cancer (SCLC), mesothelioma, hepatocellular carcinoma, prostate cancer, multiple myeloma, and combinations of said cancers.

In some embodiments, the subject has a cancer selected from diffuse large B-cell lymphoma (DLBCL), head and neck squamous cell carcinoma (HNSCC), cervical carcinoma, melanoma, colorectal carcinoma (CRC), non small-cell lung carcinoma (NSCLC), bladder carcinoma, pancreatic adenocarcinoma, small cell lung cancer (SCLC), or ovarian adenocarcinoma, and combinations of said cancers.

In some embodiments, the IDO inhibitor is administered to patients having a cancer that exhibited an inadequate response to, or progressed on, a prior treatment, e.g., a prior treatment with an immuno-oncology or immunotherapy drug, or patients having a cancer that is refractory or resistant, either intrinsically refractory or resistant (e.g., refractory to a PD-1 pathway antagonist), or a wherein the resistance or refractory state is acquired. For example, subjects who are not responsive or not sufficiently responsive to a first therapy or who see disease progression following treatment, e.g., anti-PD-1 treatment, can be treated by administration of the IDO inhibitor alone or in combination with another therapy (e.g., with an anti-PD-1 therapy).

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooks, Antisense drug Technology: Principles, strategies and applications, $2^{nd}$ Ed. CRC Press (2007) and in Ausubel et al. (1989) Current Protocols in Molecular Biology (John Wiley and Sons, Baltimore, Md.).

The following examples are offered by way of illustration and not by way of limitation.

EXAMPLES

Example 1. Antibody Generation and Screening

The lack of specific, high quality anti-IDO antibodies for Immunohistochemistry (IHC) analysis of cancer samples prompted the antibody generation and screening effort described herein. To generate anti-IDO antibodies, mice were immunized with denatured recombinant human IDO protein with a 6-His tag and thrombin site linker (His-Tb-IDO) (SEQ ID NO: 2). The protein was expressed in E. coli and purified using Ni2+ affinity and size exclusion chromatography. Purified protein was then denatured in a 0.5% SDS solution at 80° C. for 10 minutes for immunization. Four BALB/c mice were immunized with bug of the denatured protein mixed 1:1 with Ribi adjuvant (Sigma 56322) at weekly intervals through intraperitoneal, subcutaneous, and footpad injections. Serum titers were determined after six injections, and then the animals received one final intravenous and footpad boost without adjuvant three days prior to the final harvest. Both lymph nodes and spleens were harvested for subsequent hybridoma fusions 51 days after the initial immunization.

Hybridomas were generated by electrofusion with a mouse myeloma fusion partner derived from cell line P3X63AgU.1 (ATCC CRL1597) using a CytoPulse Hybrimmune large chamber cell fusion electroporator (BTX/Harvard Apparatus). Single cell suspensions of lymphocytes (fusion number 5696) and splenocytes (fusion 5697) from immunized mice were fused to an equal number of myeloma cells. Resulting cells were plated in flat bottom 96-well cell culture plates in Medium E (STEMCELL Technologies) supplemented with aminopterin (Sigma A5159) for selection of hybridomas.

After eleven days, hybridoma culture supernatants were collected and screened by direct ELISA for specific binding to denatured His-Tb-IDO. Briefly, 96-well polystyrene microplates (Corning 9018) were coated overnight at 4 C with 60 uL of denatured tagged antigen at 2 ug/mL in PBS. The plates were blocked with 200 uL/well of assay buffer containing 0.5% bovine serum albumin in PBS and washed. After the blocking step, 100 uL of supernatant from individual hybridoma culture wells were added and incubated for one hour on a plate shaker at room temperature. The plates were washed three times with PBS and 100 ul of F(ab')$_2$ fragment goat anti-mouse IgG Fcγ (1:1000 dilution) (Jackson ImmunoResearch 115-036-071) was added and incubated for 1 hour at RT and washed again with PBS. The plates were then developed with 100 ul/well of ABTS HRP substrate (Surmodics ABTS-1000-01) for 5 to 10 minutes, and analyzed using a PerkinElmer EnVision microplate reader at 405 nm. The data was analyzed using TIBCO Spotfire.

After the initial screening by ELISA, select positive supernatants were screened by IHC, as described in Example 3. IHC-positive clone 1E7 was subcloned twice and scaled-up in hybridoma culture. Harvested supernatant was purified by Protein A affinity chromatography. Purified monoclonal antibody was sterile filtered and stored at 4° C.

Total RNA was prepared from hybridoma clone 1691.5697.7G8.1E7.A1 (1E7) and heavy chain and light chain cDNAs were prepared, cloned and sequenced (FIG. 1). Antibody 1E7 comprised a heavy chain comprising the amino acid sequence set forth in SEQ ID NO: 13 and a light chain comprising the amino acid sequence set forth in SEQ ID NO: 15 (see FIG. 1 and Table 1).

TABLE 1

Sequences.

| SEQ ID | Description | Sequences |
|---|---|---|
| 1 | Human IDO | MAHAMENSWTISKEYHIDEEVGFALPNPQENLPDFYNDWMFIAKHLPDLIESG QLRERVEKLNMLSIDHLTDHKSQRLARLVLGCITMAYVWGKGHGDVRKVLPRN IAVPYCQLSKKLELPPILVYADCVLANWKKKDPNKPLTYENMDVLFSFRDGDC SKGFELVSLLVEIAAASAIKVIPTVFKAMQMQERDTLLKALLEIASCLEKALQ VEHQIHDHVNPKAFFSVLRIYLSGWKGNPQLSDGLVYEGFWEDPKEFAGGSAG QSSVFQCFDVLLGIQQTAGGGHAAQFLQDMRRYMPPAHRNFLCSLESNPSVRE FVLSKGDAGLREAYDACVKALVSLRSYHLQIVIKYILIPASQQPKENKTSEDP SKLEAKGTGGTDLMNFLKTVRSTTEKSLLKEG |
| 2 | His-Tb-IDO | MGSSHHHHHHSSGLVPRGSHMAHAMENSWTISKEYHIDEEVGFALPNPQENLP DEYNDWMFIAKHLPDLIESGQLRERVEKLNMLSIDHLTDHKSQRLARLVLGCI TMAYVWGKGHGDVRKVLPRNIAVPYCQLSKKLELPPILVYADCVLANWKKKDP NKPLTYENMDVLFSFRDGDCSKGFELVSLLVEIAAASAIKVIPTVFKAMQMQE RDILLKALLEIASCLEKALQVFHQIHDHVNPKAFFSVLRIYLSGWKGNPQLSD GLVYEGFWEDPKEFAGGSAGQSSVFQCFDVLLGIQQTAGGGHAAQFLQDMRRY MPPAHRNFLCSLESNPSVREFVLSKGDAGLREAYDACVKALVSLRSYHLQIVT KYILIPASQQPKENKTSEDPSKLEAKGIGGIDLMNFLKTVRSTTEKSLLKEG |
| 3 | IDO_1E7 VH NT | CAGGTCCAGCTTCAGCAGTCTGGGGCTGAACTGGCAAAACCTGGGGCCTCAGT GAAGATGTCCTGCAAGACTTCTGGCTACACCTTTACTAGCTACTGGATGCACT GGGTAAAACAGAGGCCTGGACAGGGTCTGGAATGGATTGGATACATTAATCCT ACCACTGGTTATACTGACTGCAATCAGAAGTTCAAGGACAAGGCCACATTGAC TGCAGACAAGTCCTCCAACACAGCCTACTTGCAACTGAGCAGCCTGACATCTG AGGACTCTGCAGTCTATTACTGTGCCAGATCGGCTATGTTTGGTAGGGGGTGG GGCCAAGGCACCACTCTCACGGTCTCCTCA |
| 4 | IDO_1E7 VH AA | QVQLQQSGAELAKPGASVKMSCKTSGYTFTSYWMHWVKQRPGQGLEWIGYINP TTGYTDCNQKFKDKATLTADKSSNTAYLQLSSLTSEDSAVYYCARSAMFGRGW GQGTTLTVSS |
| 5 | IDO_1E7 VL NT | GATGTTGTGATGACCCAGACTCCACTCACTTTGTCGGTTACCATTGGACAACC AGCCTCCATCTCTTGCAAGTCAAGTCAGAGCCTCTTACATAGTGATGGAAAGA CATATTTGAATTGGTTGTTACAGAGGCCAGGCCAGTCTCCAAAGCGCCTAATC TATCTGGTGTCTAAACTGGACTCTGGAGTCCCTGACAGGTTCACTGGCAGTGG ATCAGGGACAGATTTCACACTGAAAATCAGCAGAGTGGAGGCTGAGGATTTGG GAGTTTATTATTGTTGGCAAGGTACACATTTTCCTCAGACGTTCGGTGGAGGC TCCAAGCTGGAAATCAAA |

TABLE 1-continued

Sequences.

| SEQ ID | Description | Sequences |
|---|---|---|
| 6 | IDO_1E7 VL AA | DVVMTQTPLTLSVTIGQPASISCKSSQSLLHSDGKTYLNWLLQRPGQSPKRLI YLVSKLDSGVPDRFTGSGSGTDFTLKISRVEAEDLGVYYCWQGTHFPQTFGGG SKLEIK |
| 7 | IDO_1E7 VH_CDR1 | SYWMH |
| 8 | IDO_1E7 VH_CDR2 | YINPTTGYTDCNQKFKD |
| 9 | IDO_1E7 VH_CDR3 | SAMFGRG |
| 10 | IDO_1E7 VL_CDR1 | KSSQSLLHSDGKTYLN |
| 11 | IDO_1E7 VL_CDR2 | LVSKLDS |
| 12 | IDO_1E7 VL_CDR3 | WQGTHFPQT |
| 13 | IDO_1E7 Heavy Chain AA | QVQLQQSGAELAKPGASVKMSCKTSGYTFTSYWMHWVKQRPGQGLEWIGYINP TTGYTDCNQKFKDKATLTADKSSNTAYLQLSSLTSEDSAVYYCARSAMFGRGW GQGTTLIVSSAKTIPPSVYPLAPGSAAQINSMVTLGCLVKGYFPEPVTVTWNS GSLSSGVHTFPAVLQSDLYTLSSSVTVPSSTWPSETVTCNVAHPASSTKVDKK IVPRDCGCKPCICTVPEVSSVFIFPPKPKDVLTITLTPKVICVVVDISKDDPE VQFSWFVDDVEVHTAQTQPREEQFNSTFRSVSELPIMHQDWLNGKEFKCRVNS AAFPAPIEKTISKTKGRPKAPQVYTIPPPKEQMAKDKVSLTCMITDFFPEDIT VEWQWNGQPAENYKNTQPIMDTDGSYFVYSKLNVQKSNWEAGNTFTCSVLHEG LHNHHTEKSLSHSPG |
| 14 | IDO_1E7 Heavy Chain NT | CAGGTCCAGCTTCAGCAGTCTGGGGCTGAACTGGCAAAACCTGGGGCCTCAGT GAAGATGTCCTGCAAGACTTCTGGCTACACCTTTACTAGCTACTGGATGCACT GGGTAAAACAGAGGCCTGGACAGGGTCTGGAATGGATTGGATACATTAATCCT ACCACTGGTTATACTGACTGCAATCAGAAGTTCAAGGACAAGGCCACATTGAC TGCAGACAAGTCCTCCAACACAGCCTACTTGCAACTGAGCAGCCTGACATCTG AGGACTCTGCAGTCTATTACTGTGCCAGATCGGCTATGTTTGGTAGGGGTGG GGCCAAGGCACCACTCTCACGGTCTCCTCAGCTAAAACGACACCCCCATCTGT CTATCCGCTGGCCCCTGGATCCGCTGCCCAAACTAACTTCCATGGTGACCCTGG GATGCCTGGTCAAGGGCTATTTCCCTGAGCCAGTGACAGTGACCTGGAACTCT GGCTCCCTGTCCAGCGGTGTGCACACCTTCCCAGCTGTCCTGCAGTCTGACCT CTACACTCTGAGCAGCTCAGTGACTGTCCCCTCCAGCACCTGGCCCAGCGAGA CCGTCACCTGCAACGTTGCCCACCCGGCCAGCAGCACCAAGGTGGACAAGAAA ATTGTGCCCAGGGATTGTGGTTGTAAGCCTTGCATATGTACAGTCCCAGAAGT ATCATCTGTCTTCATCTTCCCCCCAAAGCCCAAGGATGTGCTCACCATTACTC TGACTCCTAAGGTCACGTGTGTTGTGGTAGACATCAGCAAGGATGATCCCGAG GTCCAGTTCAGCTGGTTTGTAGATGATGTGGAGGTGCACACAGCTCAGACGCA ACCCCGGGAGGAGCAGTTCAACAGCACTTTCCGCTCAGTCAGTGAACTTCCCA TCATGCACCAGGACTGGCTCAATGGCAAGGAGTTCAAATGCAGGGTCAACAGT GCAGCTTTCCCTGCCCCCATCGAGAAAACCATCTCCAAAACCAAAGGCAGACC GAAAGGCTCCACAAGTCTACACCATTCCACCTCCCAAGGAGCAGATGGCCAAGG ATAAAGTCAGTCTGACCTGCATGATAACAGACTTCTTCCCTGAAGACATTACT GTGGAGTGGCAGTGGAATGGGCAGCCAGCGGAGAACTACAAGAACACTCAGCC CATCATGGACACAGATGGCTCTTACTTCGTCTACAGCAAGCTCAATGTGCAGA AGAGCAACTGGGAGGCAGGAAATACTTTCACCTGCTCTGTGTTACATGAGGGC CTGCACAACCACCATACTGAGAAGAGCCTCTCCCACTCTCCTGGT |
| 15 | IDO_1E7 Light Chain AA | DVVMTQTPLTLSVTIGQPASISCKSSQSLLHSDGKTYLNWLLQRPGQSPKRLI YLVSKLDSGVPDRFTGSGSGTDFTLKISRVEAEDLGVYYCWQGTHFPQTFGGG SKLEIKRADAAPTVSIFPPSSEQLTSGGASVVCFLNNFYPKDINVKWKIDGSE RQNGVLNSWIDQDSKDSTYSMSSTLTLIKDEYERHNSYTCEATHKTSTSPIVK SFNRNEC |
| 16 | IDO_1E7 Light Chain NT | GATGTTGTGATGACCCAGACTCCACTCACTTTGTCGGTTACCATTGGACAACC AGCCTCCATCTCTTGCAAGTCAAGTCAGAGCCTCTTACATAGTGATGGAAAGA CATATTTGAATTGGTTGTTACAGAGGCCAGGCCAGTCTCCAAAGCGCCTAATC TATCTGGTGTCTAAACTGGACTCTGGAGTCCCTGACAGGTTCACTGGCAGTGG ATCAGGGACAGATTTCACACTGAAAATCAGCAGAGTGGAGGCTGAGGATTTGG GAGTTTATTATTGTTGGCAAGGTACACATTTTCCTCAGACGTTCGGTGGAGGC TCCAAGCTGGAAATCAAACGGGCTGATGCTGCACCAACTGTATCCATCTTCCC ACCATCCAGTGAGCAATTGACATCTGGAGGTGCCTCAGTCGTGTGCTTCTTGA ACAACTTCTACCCCAAAGACATCAATGTCAAGTGGAAGATTGATGGCAGTGAA CGACAAAATGGCGTCCTGAACAGTTGGACCGATCAGGACAGCAAAGACAGCAC |

TABLE 1-continued

Sequences.

| SEQ ID | Description | Sequences |
|---|---|---|
| | | CTACAGCATGAGCAGCACCCTCACGTTGACCAAGGACGAGTATGAACGACATA ACAGCTATACCTGTGAGGCCACTCACAAGACATCAACTTCACCCATTGTCAAG AGCTTCAACAGGAATGAGTGT |

Example 2. Recombinant Antibody Production and Purification

The anti-IDO antibody described herein can be expressed using cloning and recombinant expression techniques commonly available in the art. For example, the recombinant monoclonal antibody 1E7 was produced by transient expression in HEK-293-6E cells. Briefly, endotoxin-free mammalian expression plasmids encoding the antibody heavy and light chain were co-transfected into log phase HEK-293-6E cells using 293fectin transfection reagent (ThermoFisher). Transfected cells were cultured in serum-free FreeStyle 293 expression medium (ThermoFisher) in a humidified 37° C. $CO_2$ shaker incubator for 5 days. Culture supernatant was collected by centrifugation of cell suspension. Recombinant antibody present in the supernatant was purified by standard protein A column chromatography. After binding and washing, bound antibody was eluted by low pH citrate buffer from the column and immediately adjusted to neutral pH. The antibody solution was then dialyzed in sterile PBS buffer, concentrated and sterile-filtered. The final purified antibody was quantified at OD280 nm and analyzed by SDS-PAGE for purity. The antibody activity was validated by antigen specific ELISA assay using reference antibody as standard.

Example 3. Immunohistochemistry Assay to Asses IDO Expression in Cancers

Immunohistochemistry (IHC) is a useful tool for studying IDO expression in cancer tissues. Formalin Fixed Paraffin Embedded (FFPE) tissue is currently the primary format of pathology tissue samples in clinical settings. To explore which tumor types or clinical settings are more likely to respond to IDO inhibitor therapy, an IHC assay suitable for FFPE samples is required to assess IDO expression in situ.

Fifty positive supernatants derived from 3 hybridoma fusions were screened by IHC using custom-made low density FFPE TMA (tissue micro-array) that consists of positive (human IDO transfected HEK 293 cells) and negative control cells (non-transfected HEK293 cells) and tissues (IDO mRNA low, moderate, or high expressing tumor samples verified by in situ hybridization using RNAscope). Through two rounds of screening and subcloning, 6 purified clones were selected for assay development and validation. Monoclonal antibody 1E7, a mouse IgG1, was identified as the lead antibody for IHC.

To further develop a user and clinical friendly assay, mAb 1E7 was optimized for automated IHC using the Leica BondRX platform. The Bond Polymer Refine Detection System (Leica, catalog #DS9800) was used for the detection of IDO1 and all incubations were carried out at room temperature. Briefly, slides were deparaffinized and rehydrated following routine histology procedures. The slides were loaded onto the Leica BondRX automated IHC stainer and antigen retrieved with either the Bond Epitope Retrieval Solution 1 (Leica, catalog #AR9961) or 2 (Leica, catalog #AR9640) for 20 minutes at 95° C. Peroxidase block from the Bond Polymer Refine Detection kit (Leica, catalog #DS9800) was applied to the slides for 10 min, followed by non-specific binding blocking using protein block (Agilent-DAKO, catalog #X0909) supplemented with 0.5% human gamma globulins (Sigma, catalog #G-4386) for 20 min. Primary antibody 1E7 was incubated at 0.03 or 0.05 µg/ml for 60 minutes, and followed by rabbit anti-mouse linker and then anti-rabbit Poly-HRP-IgG from the Bond Polymer Refine Detection Kit for 30 min each step. Finally, the slides were reacted with the DAB substrate-chromogen solution from the Bond Polymer Refine Detection Kit for 6 min. The slides were then counterstained with hematoxylin, dehydrated, cleared, and coverslipped with Permount or DePeX following routine histological procedure. Protein block was used as diluent for the primary antibody. Mouse monoclonal IgG1 (Agilent-DAKO, catalog #X0931) was used as isotype control. Whole slide digital images of stained slides were captured and viewed using Aperio AT2 ScanScope and e-Slide Manager (Leica), and then analyzed by a pathologist for manual score or with Halo software (Indica) for quantitative image analysis.

Results: In HEK293 cells transfected with human IDO1, strong positive staining by antibody 1E7 was observed in the vast majority of the cells and no staining in non-transfected HEK293 cells (FIG. 2, panels A and B). Positive staining was observed in H1048 cells (FIG. 2, panel C), which is an IDO1 low/moderate endogenous-expressing cell line. However, H1048 cells whose IDO1 was knocked out by CRISPR exhibited an about 90% reduction of the positive staining (FIG. 2, panel D). In addition, positive staining was observed in cervical cancer cells and tumor associated immune cells (FIG. 2, panel E). The positive staining was displaced by added IDO1 protein (FIG. 2, panel F). These data indicated that mAb 1E7 was specific for IDO1. Furthermore, the comparison of mAb 1E7 and commercial mAb D5J4E in H1048 cells and cervical squamous carcinoma sample showed that 1E7 had a significantly higher sensitivity than D5J4E (FIG. 3, A-H).

Ten tumor types were evaluated for presence of IDO1 positive staining in tumor cells and/or tumor associated immune cells (TAICs), using IHC with mAb 1E7. In general, the expression of IDO1 positive TAICs was broadly distributed across tumor types, and IDO1 positive cells was observed in all samples examined, with TAICs most often being predominantly within the tumor stroma. Based on morphology, the IDO1-positive TAICs was primarily in dendritic/macrophage-like cells, with no notable staining in lymphocytes. Similarly, in samples with clearly visible lymphoid aggregates or tumor associated tertiary lymphoid structures, IDO1 positive staining was observed primarily in the dendritic/macrophage-like cells but not lymphocytes. Among the 10 tumor types evaluated, DLBCL had the most abundant IDO1 positive TAICs. Melanomas, cervical carcinomas and HNSCC also had high numbers of IDO1-positive TAICs, while SCLC and ovarian carcinoma had the lowest level of IDO1-positive TAICs (FIG. 4). In order of highest to lowest IDO1-positive TAIC frequency, the tumor cohorts ranked as follows: diffuse large B-cell lymphoma (DLBCL); head and neck squamous cell carcinoma (HNSCC); cervical carcinoma; melanoma; colorectal carcinoma (CRC); non small-cell lung carcinoma (NSCLC); bladder carcinoma; pancreatic adenocarcinoma; small cell lung cancer (SCLC), and ovarian adenocarcinoma (FIG. 4).

In addition to expression in TAICs, IDO1 positive staining was also observed in subset of tumor cells in most tumor types. The positive staining in tumor cells displayed a predominantly cytoplasmic pattern. Among the 10 tumor types examined, cervical carcinoma had the highest expression of IDO1 while SCLC showed the lowest expression, with only one sample showing weak cytoplasmic staining in a very small number of tumor cells (FIG. 5). In order of highest to lowest cytoplasmic H score, the tumor cohorts ranked as follows: cervical carcinoma; HNSCC; NSCLC; bladder carcinoma; ovarian adenocarcinoma; CRC; melanoma; pancreatic adenocarcinoma; DLBCL; and SCLC (FIG. 5).

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All publications, patents, and patent applications disclosed herein are incorporated by reference to the same extent as if each individual publication, patent or patent application was specifically and individually indicated to be incorporated by reference.

What is claimed:

1. An antibody that specifically binds to human Indoleamine 2,3-dioxygenase (IDO), comprising a heavy chain variable region (VH) and a light chain variable region (VL); wherein the VH comprises a VH complementarity determining region (CDR) 1 (VH-CDR1), a VH-CDR2, and a VH-CDR3 and the VL comprises a VL-CDR1, a VL-CDR2, and a VL-CDR3; wherein the VH-CDR1 comprises the amino acid sequence set forth in SEQ ID NO:7, the VH-CDR2 comprises the amino acid sequence set forth in SEQ ID NO:8, the VH-CDR3 comprises the amino acid sequence set forth in SEQ ID NO:9, the VL-CDR1 comprises the amino acid sequence set forth in SEQ ID NO: 10, the VL-CDR2 comprises the amino acid sequence set forth in SEQ ID NO: 11, and the VL-CDR3 comprises the amino acid sequence set forth in SEQ ID NO:12.

2. The antibody of claim 1, wherein the VH comprises an amino acid sequence having at least about 80%, at least about 90%, at least about 95%, at least about 96%, at least about 97%, at least about 98%, or at least about 99% sequence identity to the amino acid sequence set forth in SEQ ID NO: 4.

3. The antibody of claim 1, wherein the VH comprises an amino acid sequence having at least about 98% sequence identity to the amino acid sequence set forth in SEQ ID NO: 4.

4. The antibody of claim 1, wherein the VH comprises an amino acid sequence having at least about 99% sequence identity to the amino acid sequence set forth in SEQ ID NO: 4.

5. The antibody of claim 1, wherein the VH comprises the amino acid sequence set forth in SEQ ID NO: 4.

6. The antibody of claim 1, wherein the VL comprises an amino acid sequence having at least about 80%, at least about 90%, at least about 95%, at least about 96%, at least about 97%, at least about 98%, or at least about 99% sequence identity to the amino acid sequence set forth in SEQ ID NO: 6.

7. The antibody of claim 1, wherein the VL comprises an amino acid sequence having at least about 98% sequence identity to the amino acid sequence set forth in SEQ ID NO: 6.

8. The antibody of claim 1, wherein the VL comprises an amino acid sequence having at least about 99% sequence identity to the amino acid sequence set forth in SEQ ID NO: 6.

9. The antibody of claim 1, wherein the VL comprises the amino acid sequence set forth in SEQ ID NO: 6.

10. An antibody that specifically binds to human Indoleamine 2,3-dioxygenase (IDO), comprising a heavy chain variable region (VH) and a light chain variable region (VL), wherein the VH comprises the amino acid sequence of SEQ ID NO: 4, and the VL comprises the amino acid sequence set forth in SEQ ID NO: 6.

11. The antibody of claim 1, wherein the antibody comprises a heavy chain comprising an amino acid sequence having at least about 80%, at least about 90%, at least about 95%, at least about 96%, at least about 97%, at least about 98%, or at least about 99% sequence identity to the amino acid sequence set forth in SEQ ID NO: 13.

12. The antibody of claim 1, wherein the antibody comprises a heavy chain comprising an amino acid sequence having at least about 98% sequence identity to the amino acid sequence set forth in SEQ ID NO: 13.

13. The antibody of claim 1, wherein the antibody comprises a heavy chain comprising an amino acid sequence having at least about 99% sequence identity to the amino acid sequence set forth in SEQ ID NO: 13.

14. The antibody of claim 1, wherein the antibody comprises a heavy chain comprising the amino acid sequence set forth in SEQ ID NO: 13.

15. The antibody of claim 1, wherein the antibody comprises a light chain comprising an amino acid sequence having at least about 80%, at least about 90%, at least about 95%, at least about 96%, at least about 97%, at least about 98%, or at least about 99% sequence identity to the amino acid sequence set forth in SEQ ID NO: 15.

16. The antibody of claim 1, wherein the antibody comprises a light chain comprising an amino acid sequence having at least about 98% sequence identity to the amino acid sequence set forth in SEQ ID NO: 15.

17. The antibody of claim 1, wherein the antibody comprises a light chain comprising an amino acid sequence having at least about 99% sequence identity to the amino acid sequence set forth in SEQ ID NO: 15.

18. The antibody of claim 1, wherein the antibody comprises a light chain comprising the amino acid sequence set forth in SEQ ID NO: 15.

19. An antibody that specifically binds to human Indoleamine 2,3-dioxygenase (IDO), comprising a heavy chain comprising the amino acid sequence set forth in SEQ ID NO: 13 and a light chain comprising the amino acid sequence set forth in SEQ ID NO: 15.

20. The antibody of claim 1, wherein the antibody is capable of specifically staining IDO in a biological sample by immunohistochemistry (IHC).

21. The antibody of claim 1, wherein the antibody is capable of specifically staining IDO in a cancer sample by immunohistochemistry (IHC).

22. The antibody of claim 1, wherein the antibody is capable of specifically staining IDO in a FFPE (formalin fixed paraffin embedded) cancer sample by IHC.

23. The antibody of claim 1, wherein the antibody is an IgG1, an IgG2, an IgG3, an IgG4 or a variant thereof, or wherein the antibody is an IgG1, an IgG2a, an IgG2b, an IgG3 or a variant thereof.

24. The antibody of claim 1, wherein the antibody is an IgG1 antibody.

25. A polynucleotide encoding the antibody of claim 1.

26. A vector comprising the polynucleotide of claim 25.

27. A host cell comprising the antibody of claim 1.

28. A method of producing an antibody comprising culturing the host cell of claim 27 so that the antibody is produced.

29. An immunoconjugate comprising the antibody of claim 1 and an agent.

30. The immunoconjugate of claim 29, wherein the agent is selected from the group consisting of a label, a cytotoxic agent, an imaging agent, a second antibody, an enzyme, and any combination thereof.

31. A pharmaceutical composition comprising the antibody of claim 1, and a pharmaceutically acceptable carrier.

32. A method of detecting human IDO in a biological sample comprising contacting the biological sample with the antibody of claim 1 under conditions permissive for binding of the antibody to human IDO, and detecting binding between the antibody and human IDO in the biological sample.

33. The method of claim 32, wherein the biological sample is cancer sample.

34. The method of claim 33, wherein the biological sample selected from a diffuse large B-cell lymphoma (DLBCL) sample; a head and neck squamous cell carcinoma (HNSCC) sample; a cervical carcinoma sample; a melanoma sample; a colorectal carcinoma (CRC) sample; a non small-cell lung carcinoma (NSCLC) sample; a bladder carcinoma sample; a pancreatic adenocarcinoma sample; a small cell lung cancer (SCLC) sample; and an ovarian adenocarcinoma sample.

35. A method of identifying a cancer patient having an IDO-positive cancer, comprising contacting a cancer sample from the patient with the anti-IDO antibody of claim 1 under conditions permissive for binding of the anti-IDO antibody to human IDO, and detecting binding between the anti-IDO antibody and human IDO in the cancer sample.

\* \* \* \* \*